United States Patent
Zhou et al.

(10) Patent No.: US 11,965,862 B1
(45) Date of Patent: Apr. 23, 2024

(54) FATIGUE BENDING AND FOLDING TEST DEVICE FOR ULTRA-THIN METAL STRIP

(71) Applicant: Taiyuan University of Science and Technology, Taiyuan (CN)

(72) Inventors: Cunlong Zhou, Taiyuan (CN); Dong Wei, Taiyuan (CN); Shijie Sun, Taiyuan (CN); Guodong Li, Taiyuan (CN); Yijing Meng, Taiyuan (CN)

(73) Assignee: Taiyuan University of Science and Technology, Taiyuan (CN)

( * ) Notice: Subject to any disclaimer, the term of this patent is extended or adjusted under 35 U.S.C. 154(b) by 0 days.

(21) Appl. No.: 18/536,298

(22) Filed: Dec. 12, 2023

(30) Foreign Application Priority Data

Dec. 12, 2022 (CN) ......................... 202211610570.3

(51) Int. Cl.
  *G01N 3/20*  (2006.01)
  *G01N 3/06*  (2006.01)
  *G01N 33/20*  (2019.01)

(52) U.S. Cl.
  CPC ............... *G01N 3/20* (2013.01); *G01N 3/066* (2013.01); *G01N 33/20* (2013.01)

(58) Field of Classification Search
  CPC ........... G01N 3/20; G01N 3/066; G01N 33/20
  See application file for complete search history.

(56) References Cited

U.S. PATENT DOCUMENTS

| 11,761,867 B2* | 9/2023 | Joyce | G01N 3/34 73/854 |
| 2021/0341367 A1* | 11/2021 | Joyce | G01N 3/04 |
| 2021/0348995 A1* | 11/2021 | Kim | G01N 3/20 |
| 2022/0163435 A1* | 5/2022 | Park | G01N 3/20 |
| 2022/0357255 A1* | 11/2022 | Levesque | G01N 3/34 |

FOREIGN PATENT DOCUMENTS

| CN | 110296814 A * | 10/2019 | G01M 11/00 |
| WO | WO-2019041546 A1 * | 3/2019 | G01M 99/007 |

\* cited by examiner

*Primary Examiner* — Jonathan M Dunlap
(74) *Attorney, Agent, or Firm* — MATTHIAS SCHOLL P.C.; Matthias Scholl

(57) ABSTRACT

A fatigue bending and folding test device for an ultra-thin metal strip, including: a first driver module, a first folding module, a first diameter adjustment module, an expansion module, and a frame. The first driver module, the first folding module, the first diameter adjustment module, and the expansion module are all disposed on the frame. The first driver module includes a servo motor, a coupler, and a drive gearbox; the drive gearbox includes a driving gear shaft, a driven gear shaft, a plurality of output end covers, and a plurality of bearings. The first folding module includes an upper folding member, a lower folding member, and a first mounting base. The first clamping member includes a sliding block, a lower clamping plate, an upper clamping plate, a rotating shaft, an intermediate pressure plate, and a plurality of fixing bolts.

9 Claims, 33 Drawing Sheets

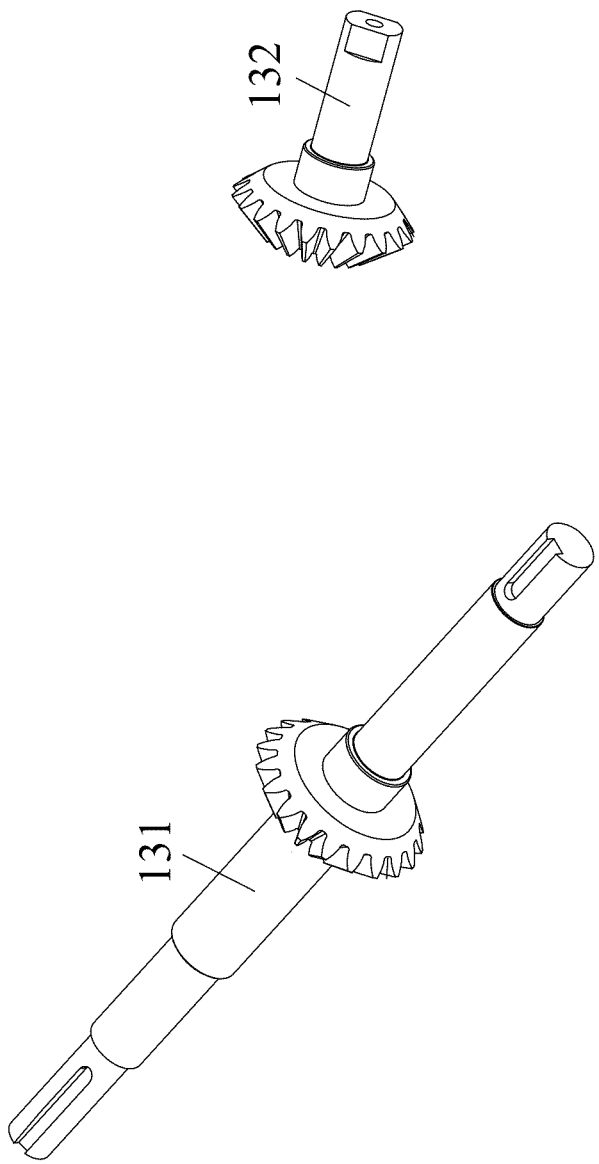
FIG. 4A
FIG. 4B
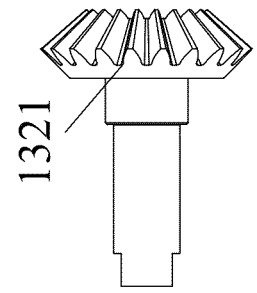
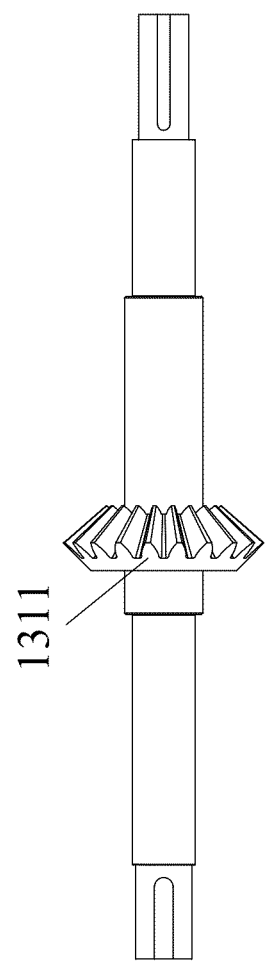
FIG. 4C
FIG. 4D

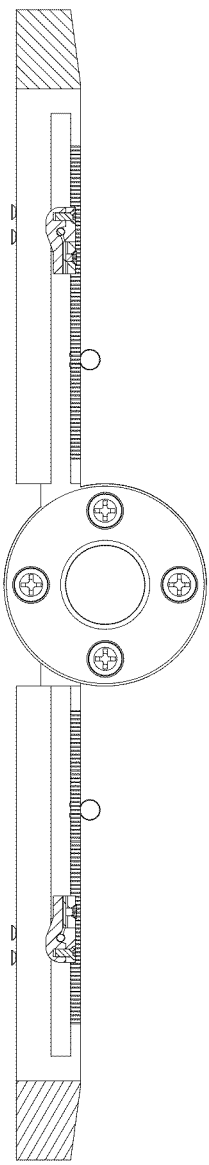
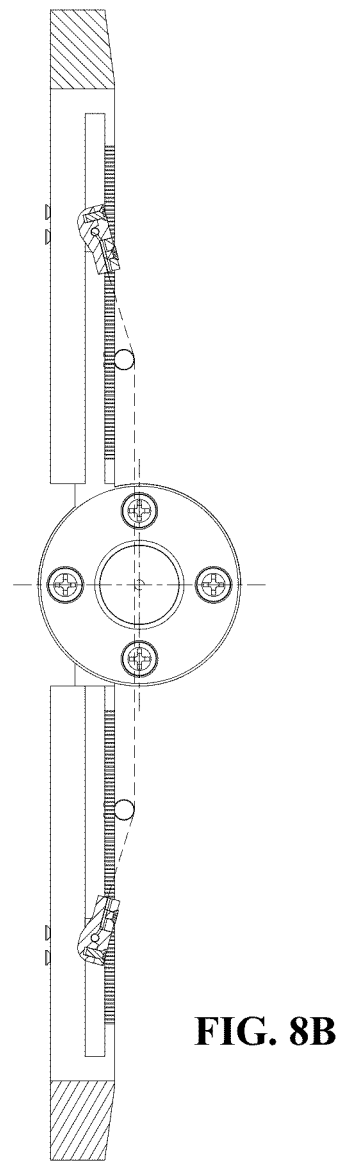
FIG. 8A  FIG. 8B
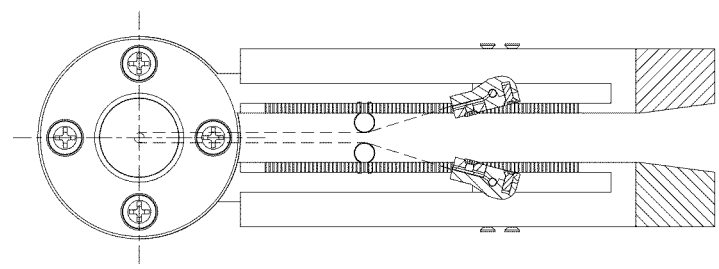
FIG. 8C

FATIGUE BENDING AND FOLDING TEST DEVICE FOR ULTRA-THIN METAL STRIP

CROSS-REFERENCE TO RELATED APPLICATIONS

Pursuant to 35 U.S.C. § 119 and the Paris Convention Treaty, this application claims foreign priority to Chinese Patent Application No. 202211610570.3 filed Dec. 12, 2022, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to a fatigue bending and folding test device for an ultra-thin metal strip.

In the flexible screen technology, the ultra-thin metal strip is used as a substrate of the screen. In case of high-frequency bending of the screen, the ultra-thin metal strip of the substrate tends to fracture because of fatigue, which means the life of the screen ends. To enhance the life of the flexible screen, it is necessary to carry out a large number of fatigue bending tests on the newly-designed ultra-thin metal strips.

Existing fatigue bending and folding equipment is mostly for the overall fatigue bending and folding tests of a flexible screen, not for that of the ultra-thin metal substrate. Because the flexible screen is made of a variety of non-metallic materials and thin metal strips through compression molding, the materials have a certain protective effect on the thin metal strips, conventional tests cannot reflect the real fatigue life of the thin metal strip.

SUMMARY

To solve the above-mentioned problems, the disclosure provides a fatigue bending and folding test device for an ultra-thin metal strip, the device comprising: a first driver module, a first folding module, a first diameter adjustment module, an expansion module, and a frame.

The first driver module, the first folding module, the first diameter adjustment module, and the expansion module are all disposed on the frame;

the first driver module comprises a servo motor, a coupler, and a drive gearbox; the drive gearbox comprises a driving gear shaft, a driven gear shaft, a plurality of output end covers, and a plurality of bearings; the drive gearbox is a hollow cubic structure comprising four sidewalls with holes, and the driving gear shaft and the driven gear shaft are disposed through the holes; the bearings are respectively disposed in the holes, and the output end covers are respectively disposed outside the holes; the bearings are configured to reduce friction between the drive/driven gear shaft and the drive gearbox, and the output end covers are fixedly connected to the bearings, respectively; the driving gear shaft is one in number and long, and the driven gear shaft is two in number and short; two ends of the driving gear shaft pass through two holes of the drive gearbox, respectively; two short driven gear shafts are vertically arranged on both sides of the driving gear shaft and pass through other two holes of the drive gearbox, respectively; the servo motor is in transmission connection to one end of the driving gear shaft of the drive gearbox through the coupler; the coupler is connected to the driving gear shaft, and the driving gear shaft and the coupler rotate together through keys and keyways, reducing relative sliding; the driving gear shaft is equipped with a driving bevel gear, and the driven gear shaft is equipped with a driven bevel gear; the driven gear shaft is driven by the driving gear shaft through gear meshing of the driving bevel gear and the driven bevel gear;

the first folding module comprises an upper folding member, a lower folding member, and a first mounting base; both the upper folding member and the lower folding member comprise a first crossbeam, a longitudinal arm, a first fixing ring, a connecting ring, a first clamping member, a first adjusting ring, a fixed pressure cover, and a first flange type self-lubricating bearing; the longitudinal arm is four in number and four longitudinal arms are perpendicularly disposed on a bottom end of the first crossbeam; the four longitudinal arms comprises a first outer arm, a first inner arm, a second inner arm, and a second outer arm in turn from one end to another end of the first crossbeam; the first fixing ring is fixedly disposed on lower ends of the first outer arm and the second outer arm of the upper folding member; the connecting ring is disposed on a lower end of the first inner arm on the upper folding member; the first fixing ring is fixedly disposed on lower ends of the first outer arm and the second outer arm of the lower folding member; the connecting ring is disposed on a lower end of the first inner arm of the lower folding member;

the first crossbeam of the lower folding member is wider than the first crossbeam of the upper folding member, so that two first fixing rings of the lower folding member are disposed outside two first fixing rings of the upper folding member; the two first fixing rings of the upper folding member and the two first fixing rings of the lower folding member overlap with each other through the rotation of the lower folding member, and the first flange type self-lubricating bearing is attached to an inner side of each of the two first fixing rings of the upper folding member; a threaded hole is disposed on an inner side of each of the two first fixing rings of the upper folding member, and the first flange type self-lubricating bearing is fixed in the threaded hole by screws;

a first side of the connecting ring of the upper folding member and the lower folding member, facing the second inner arm, comprises a square hole to receive the driven gear shaft, thereby limiting a radial rotation of the upper folding member and the lower folding member, so that the upper folding member and the lower folding member is only rotatable with one of the two driven gear shafts; the driven output shafts rotate to fold the upper folding member and lower folding member inward; the fixed pressure cover is disposed on a second side of the connecting ring of the upper folding member and the lower folding member; the fixed pressure cover, the driven output shaft, and the connecting ring are fixed together through fixing screws thus preventing an axial movement of the upper folding member and the lower folding member; the first mounting base comprises two first fixing shafts which are mutually symmetrical, and the two first fixing shafts extends outside the first fixing ring for installing folding members;

inner sides of the first outer arm and the first inner arm and inner sides of the second outer arm and the second inner arm of the upper folding member and the lower folding member are all provided with clamping grooves and L-shaped sliding grooves; a row of fixed threaded holes are disposed on back sides of the first outer arm, the first inner arm, the second outer arm, and the second inner arm, and the back sides are adjacent to the inner sides;

the first clamping member comprises a sliding block, a lower clamping plate, an upper clamping plate, a rotating shaft, an intermediate pressure plate, and a plurality of fixing bolts; upper parts of the upper clamping plate and the lower clamping plate comprise a plurality of threaded holes for fixed connection of the upper clamping plate and the lower clamping plate; a lower part of the upper clamping plate and a middle part of the lower clamping plate comprise a shaft groove for receive the rotating shaft; a lower part of the lower clamping plate comprises a plurality of threaded holes, and a bottom part of the lower clamping plate comprises a rectangular opening; the intermediate pressure plate and an ultra-thin metal strip are disposed through the rectangular opening; two ends of the rotating shaft comprise umbrella-shaped protrusions, and an inner side of the sliding block comprises an umbrella-shaped groove configured to cooperate with the umbrella-shaped protrusions at two ends of the rotating shaft to enable the rotating shaft to rotate in the sliding block; an outer side of the sliding block comprises a bulge that matches the L-shaped sliding grooves, so that the sliding block is flexibly clamped inside the L-shaped sliding grooves; the first clamping member is adjustable up and down between the first outer arm and the first inner arm, and between the second inner arm and the second outer arm according to a size requirement of the ultra-thin metal strip to be tested; sliding blocks on both sides of the first clamping member are fixed by tightening screws, thereby fixing the first clamping member; the first adjusting ring has a cross-section in the shape of an "Ω", and two ends of the first adjusting ring are respectively disposed in the clamping grooves; the first adjusting ring is adjusted according to requirements and a folding diameter of the ultra-thin metal strip to be tested;

the first diameter adjustment module comprises an adjustment plate, a folding bar, and a support base; the adjustment plate comprises two cross-shaped plates, a connecting rod, and a second fixing shaft; the connecting rod is fixedly disposed on inner centers of the two cross-shaped plates, and the second fixing shaft is fixedly disposed on outer centers of the two cross-shaped plates; the connecting rod and the second fixing shaft are coaxial; an inner side of each of four top ends of each of the two cross-shaped plates comprises a chute for receiving the folding bar; a limiting plate is movably disposed in the chute to fix the folding bar on a corresponding top end of each of the two cross-shaped plates; the second fixing shaft comprises two locking through holes perpendicular to each other to form a "+" shape, corresponding to the four top ends of each of the cross-shaped plates; the folding bar are four in number with different diameters, and comprises a first folding bar, a second folding bar, a third folding bar, and a fourth folding bar; the support base comprises a U-shaped base and two end covers; two top ends of the U-shaped base comprises two first mounting grooves, respectively, and the second fixing shaft is disposed in the two first mounting grooves; a lower part of each of the two end covers comprises a second mounting grooves, and two second mounting grooves correspond to the two first mounting grooves, respectively; a top part of each of the two end covers comprises two tap holes and a locking pin hole with the same diameter as the locking through holes for receiving a locking pin; the two end covers are fixed on the U-shaped base through tightening screws; the locking pin passes through the locking pin hole and enters one of the locking through holes of the second fixing shaft to prevent a radial rotation of the adjustment plate;

the expansion module comprises a second driver module without a servo motor, a second folding module, a second diameter adjustment module, a first expansion member and a second expansion member; the second driver module without a servo motor is in transmission connection to another end of the driving gear shaft of the drive gearbox through the coupler, so that a power of the expansion module is output forward; the first expansion member and the second expansion member each comprise an upper expansion part and a lower expansion part; the upper expansion part and the lower expansion part each comprise a second crossbeam, a third outer arm, a fourth outer arm, and a second fixing ring; the second fixing ring is fixedly disposed on lower ends of the third outer arm and the fourth outer arm; the second crossbeam of the lower expansion part is wider than the second crossbeam of the upper expansion part, so that two second fixing rings of the lower expansion part are disposed outside two second fixing rings of the upper expansion part; the two second fixing rings of the upper expansion part and the two second fixing rings of the lower expansion part overlap with each other, and a second flange type self-lubricating bearing is attached to an inner side of the two second fixing rings of the third outer arm and the fourth outer arm of the upper expansion part; a threaded hole is disposed on an inner side of each of the two second fixing rings of the upper expansion part, and the second flange type self-lubricating bearing is fixed in the threaded hole by screws; a second mounting base is disposed on an outer side of each of the two second fixing rings to fix the first expansion member and the second expansion member; the expansion module further comprises a second clamping member and a second adjusting ring which are disposed the same as that in the first folding module; the first expansion member and the second expansion member are respectively disposed on two sides of the first folding module, and are respectively fixed on corresponding second mounting bases; the upper expansion part is connected to the upper folding member through a first connection plate, and the lower expansion part is connected to the lower folding member through a second connection plate, so that the upper expansion part and the upper folding member of the first folding module rotate coaxially, and the lower expansion part and the lower folding member of the first folding module rotate coaxially, thereby achieving expansion and extension of the first folding module in two directions; and the first diameter adjustment module is disposed behind the first folding module, and an axis of the folding bar of the first folding module is coaxial to an axis of the first flange type self-lubricating bearing in the first fixing ring of the first folding module; the first diameter adjustment module is disposed between the first outer arm and the first inner arm, between the second inner arm and the second outer arm of the first folding module, and between the third outer arm and the fourth outer arm of the first expansion member and the second expansion member of the expansion module.

In a class of this embodiment, a middle part of the first crossbeam is arc-shaped to avoid the driving gear shaft and the coupler.

In a class of this embodiment, the first connection plate and the second connection plate are disposed between the first crossbeam and the second crossbeam.

In a class of this embodiment, a strain gauge is disposed inside the first diameter adjustment module to measure stress-strain data of the ultra-thin metal strip.

In a class of this embodiment, the expansion module is extended in multiple directions through couplers, and a number of extensions is limited by a number of samples to be tested and working parameters of the servo motor.

In a class of this embodiment, a control system of the servo motor of the first driver module is connected to a computer to set a folding angle and a folding speed of the ultra-thin metal strip, to complete tests under different working conditions.

In a class of this embodiment, the ultra-thin metal strip comprises a stainless steel ultra-thin strip, copper ultra-thin strip, titanium ultra-thin strip, or a composite ultra-thin strip.

In a class of this embodiment, the frame is an aluminum profile frame.

In a class of this embodiment, a cross-section of the first and second connection plate is L-shaped.

The following advantages are associated with the fatigue bending and folding test device for an ultra-thin metal strip of the disclosure.
1. The device of the disclosure can be used for different types of fatigue bending and folding control tests of ultra-thin metal strips comprising various materials under different working conditions;
2. The overall structure of the device is modular, and the parts of the device can be arbitrarily combined according to specific testing requirements; the ultra-thin mental strips with different testing requirements can be tested on one device at the same time, greatly improving the efficiency and reliability of testing;
3. The device can complete multiple fatigue bending and folding tests through a set of driving motors, thus fully utilizing energy consumption and saving energy;
4. The device is highly automated and easy to operate, can be used to improve the material testing level of ultra-thin metal strips, and also improve the quality of high-end hardware such as various flexible screens based on ultra-thin metal strips as substrates; and
5. The device is adapted to the measurement and analysis of fatigue bending and folding of ultra-thin metal strips with various thickness specifications.

BRIEF DESCRIPTION OF THE DRAWINGS

FIG. 4A is a schematic diagram of a driving gear shaft of one embodiment of the disclosure; FIG. 4B is a schematic diagram of a driven gear shaft of one embodiment of the disclosure; FIG. 4C is a schematic diagram of a driving bevel gear of one embodiment of the disclosure; FIG. 4D is a schematic diagram of a driven bevel gear of one embodiment of the disclosure;

FIG. 8A is a sectional view of a first folding module taken from line A-A in FIG. 7A; FIG. 8B is a sectional view of a first folding module taken from line A-A in FIG. 7A with an ultra-thin metal strip, and FIG. 8C is a schematic diagram of a first folding module with an ultra-thin metal strip of one embodiment of the disclosure;

Figure 1:
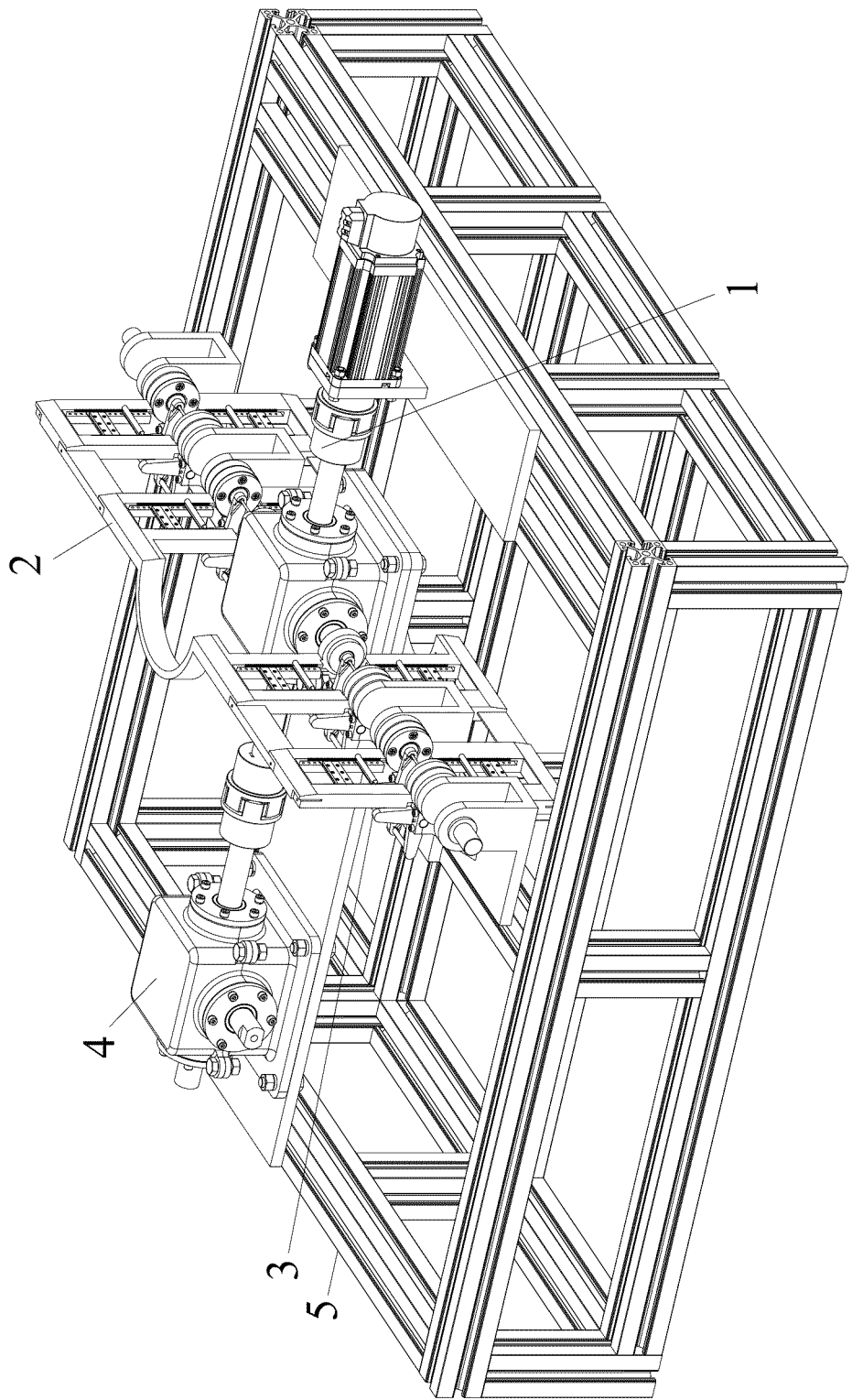
FIG. 1 is a schematic diagram of a fatigue bending and folding test device for an ultra-thin metal strip of one embodiment of the disclosure.

In the drawings, the following reference numbers are used: 1. First driver module; 11. Servo motor; 12. Coupler; 13. Drive gearbox; 131. Driving gear shaft; 132. Driven gear shaft; 133. Plurality of output end covers; 134. Plurality of bearings; 1311. Driving bevel gear; 1321. Driven bevel gear; 2. First folding module; 21. Upper folding member; 22. Lower folding member; 23. First clamping member; 24. First adjusting ring; 25. Fixed pressure cover; 26. First flange type self-lubricating bearing; 211. First crossbeam; 212. Longitudinal arm; 2121. First outer arm. 2122. First inner arm; 2123. Second inner arm; 2124. Second outer arm; 213. First fixing ring; 214. Connecting ring; 215. First mounting base; 216. Two first fixing shafts; 231. Sliding block; 232. Lower clamping plate; 233. Upper clamping plate; 234. Rotating shaft; 235. Intermediate pressure plate; 236. fixing bolts; 237. L-shaped sliding grooves; 238. Clamping grooves; 2391. First shaft groove; 2392. Second shaft groove; 240. Umbrella-shaped protrusions; 241. Umbrella-shaped groove; 3. First diameter adjustment module; 31. Adjustment plate; 311. Two cross-shaped plates; 312. Connecting rod. 313. Second fixing shaft; 314. Locking through holes; 315. Chute; 316. Limiting plate; 321. First folding bar; 322. Second folding bar; 323. Third folding bar; 324. Fourth folding bar 33. Support base; 331. U-shaped base; 332. Two end covers; 333. Tightening screws 334. Two tap holes; 335. Locking pin; 336. Locking pin hole; 337. First mounting grooves; 4. Expansion module 41. First expansion member; 42. Second expansion member; 43. Upper expansion part; 44. Lower expansion part; 45. Second crossbeam; 46. First connection plate; 5. Frame.

DETAILED DESCRIPTION

To further illustrate the disclosure, embodiments detailing a fatigue bending and folding test device for an ultra-thin metal strip are described below. It should be noted that the following embodiments are intended to describe and not to limit the disclosure.

Figure 2:
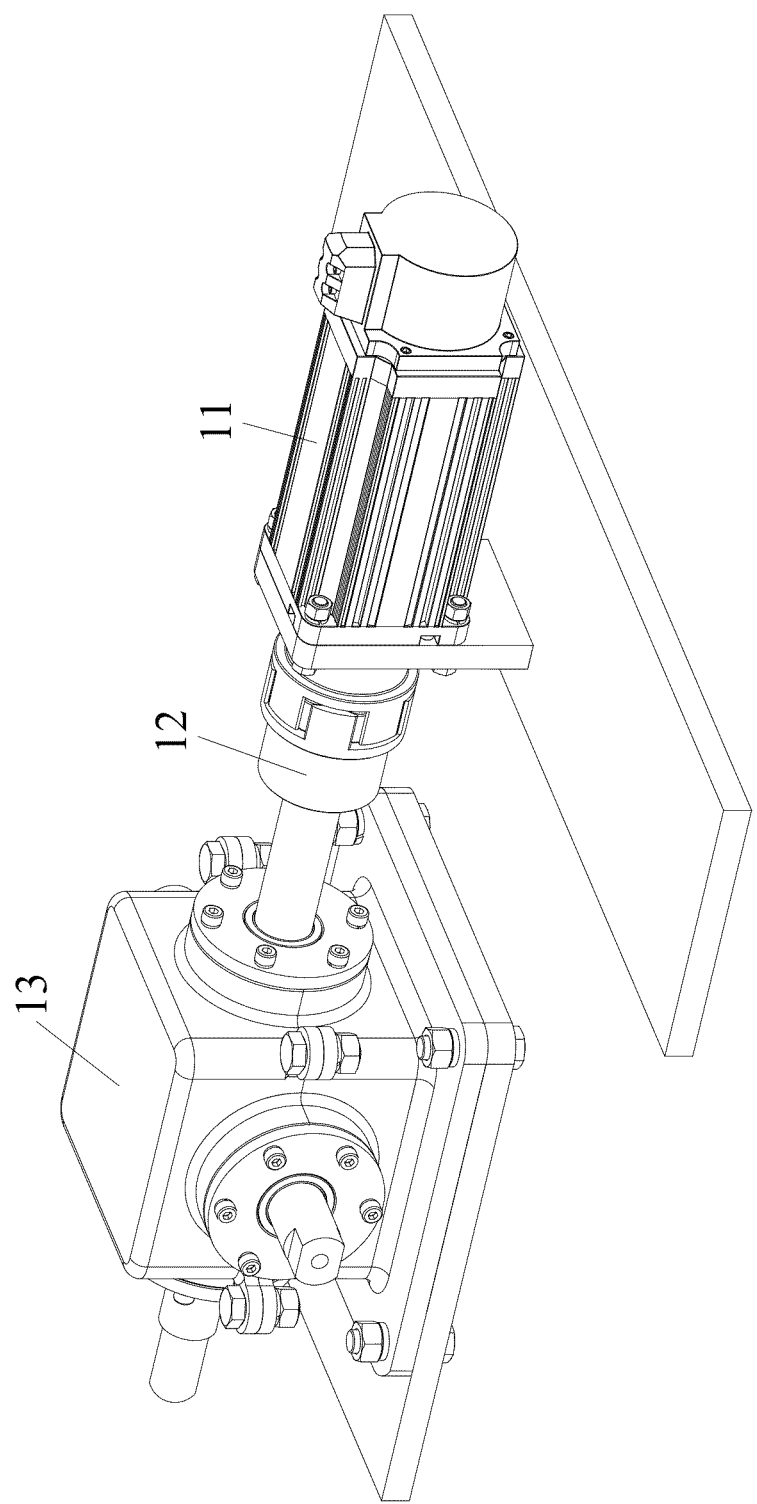
FIG. 2 is a schematic diagram of a first driver module of one embodiment of the disclosure.
Figure 3:
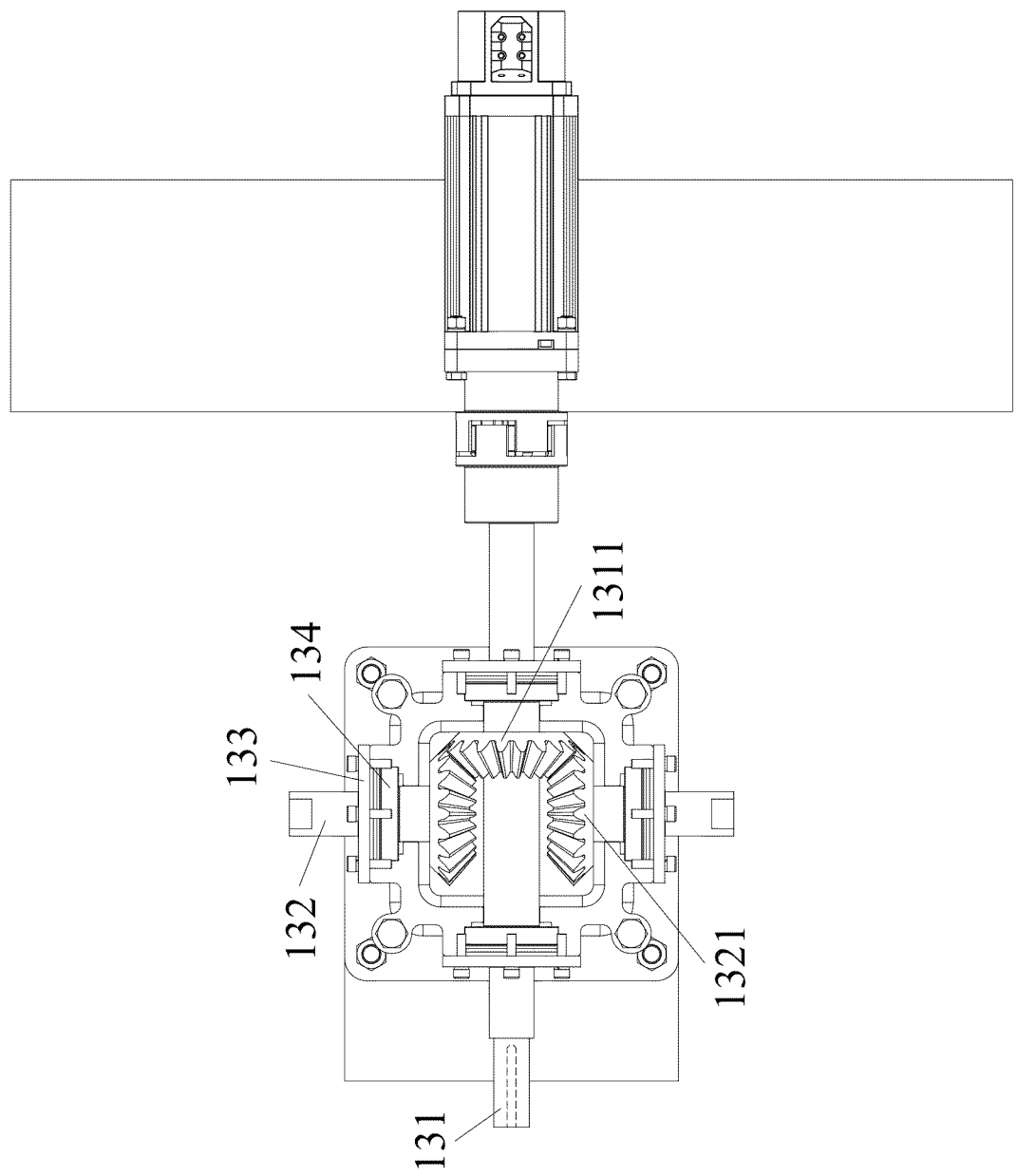
FIG. 3 is a top view of a first driver module of one embodiment of the disclosure.
Figure 5:
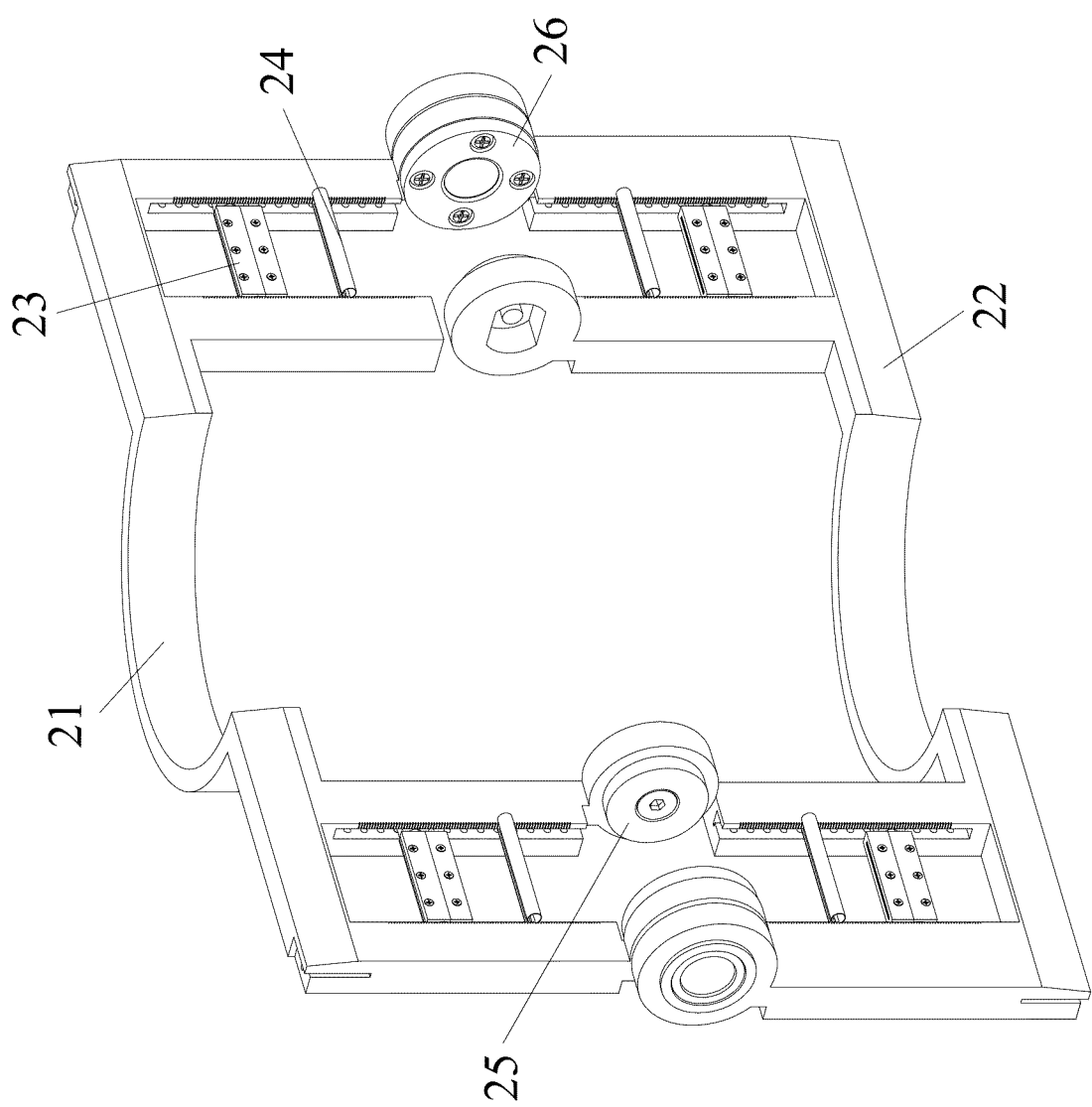
FIG. 5 is a schematic diagram of a first folding module of one embodiment of the disclosure.
Figure 6:
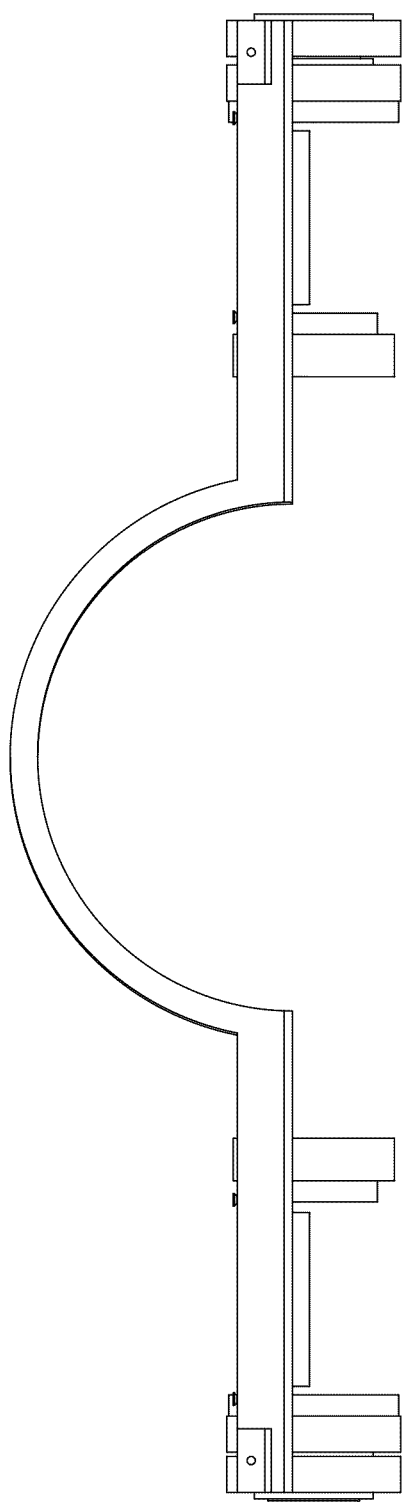
FIG. 6 is a top view of a first folding module of one embodiment of the disclosure.
Figure 7A:
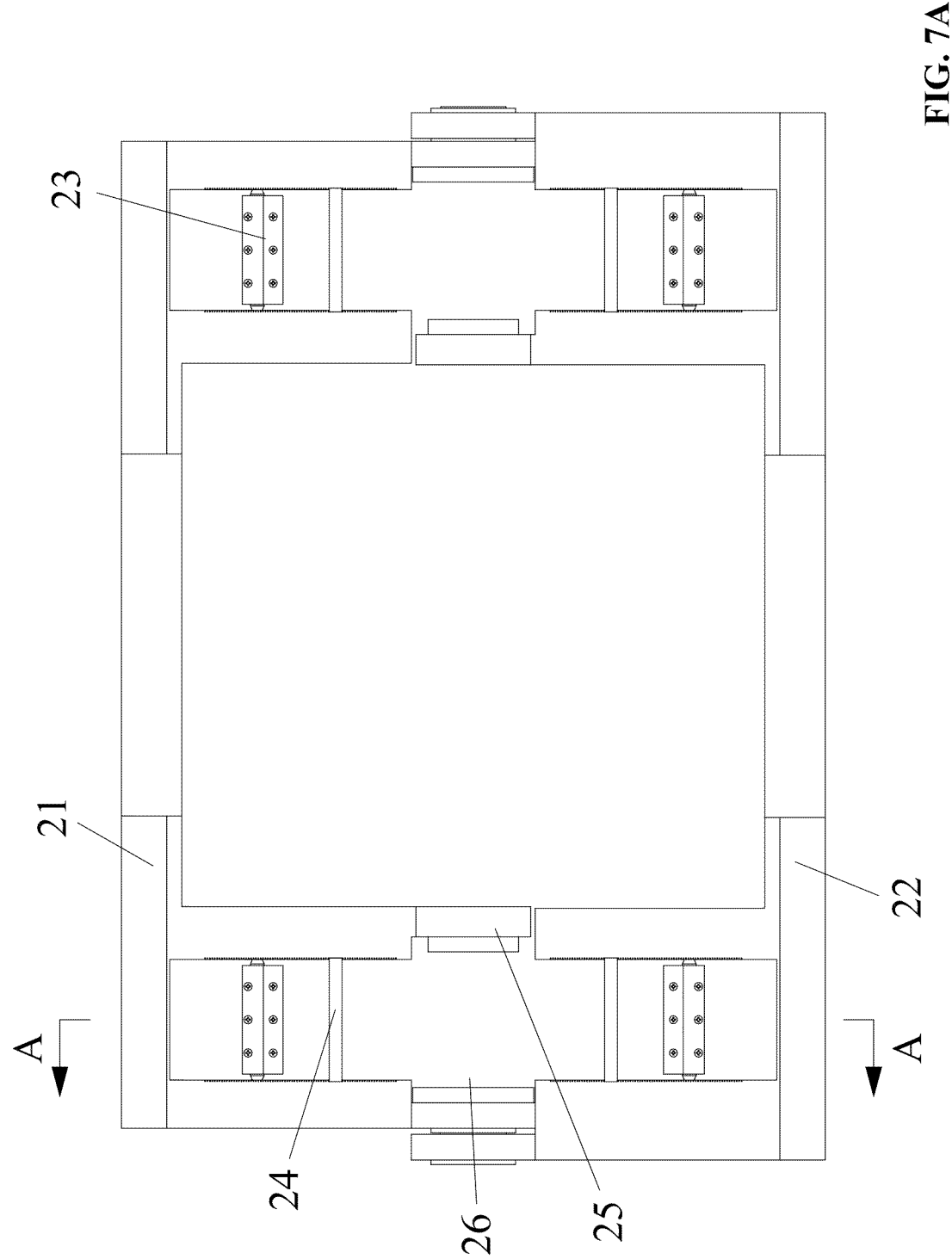
FIG. 7A is a schematic diagram of a front view of a first folding module of one embodiment of the disclosure.
Figure 7B:
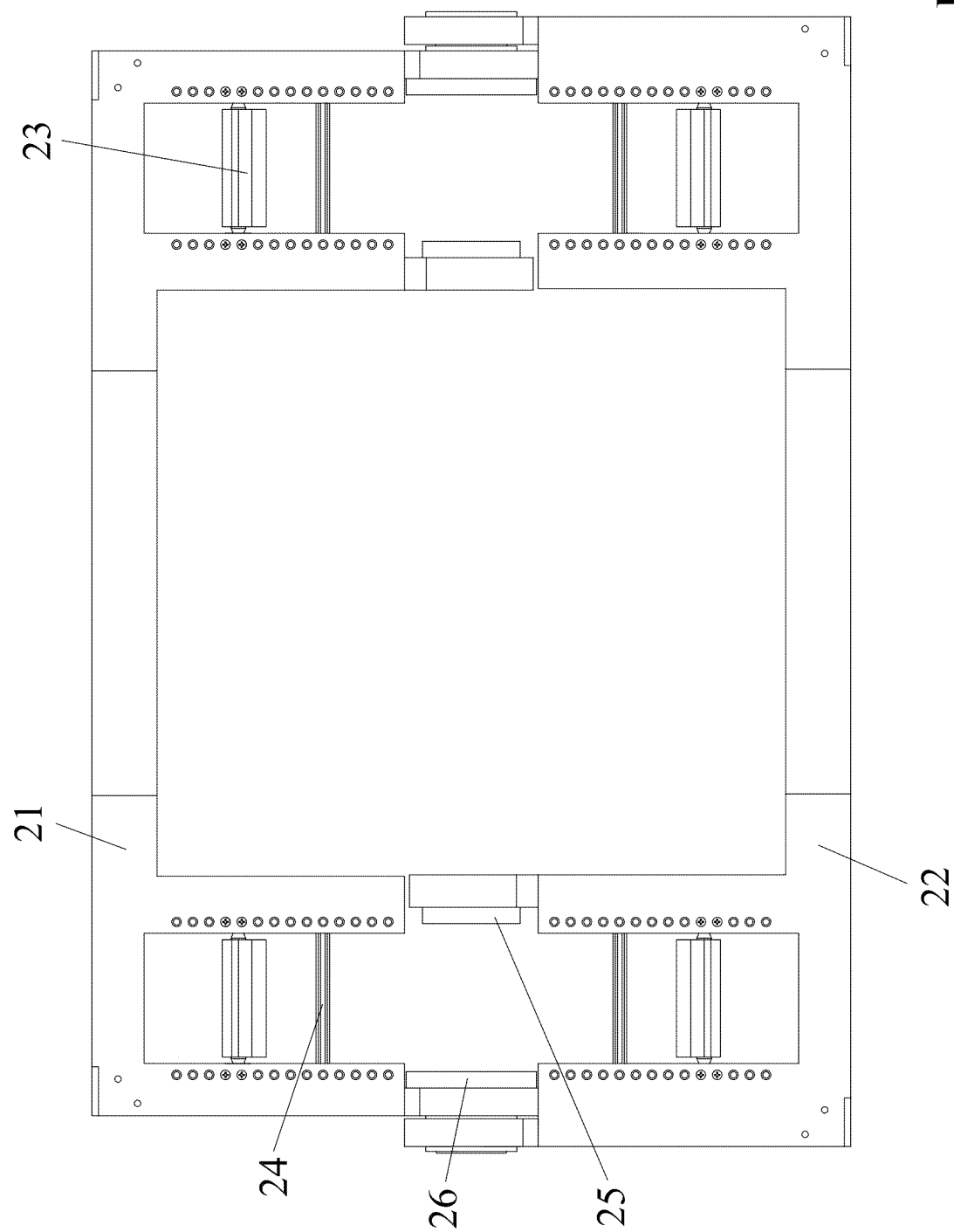
FIG. 7B is a rear view of a first folding module of one embodiment of the disclosure.
Figure 9A:
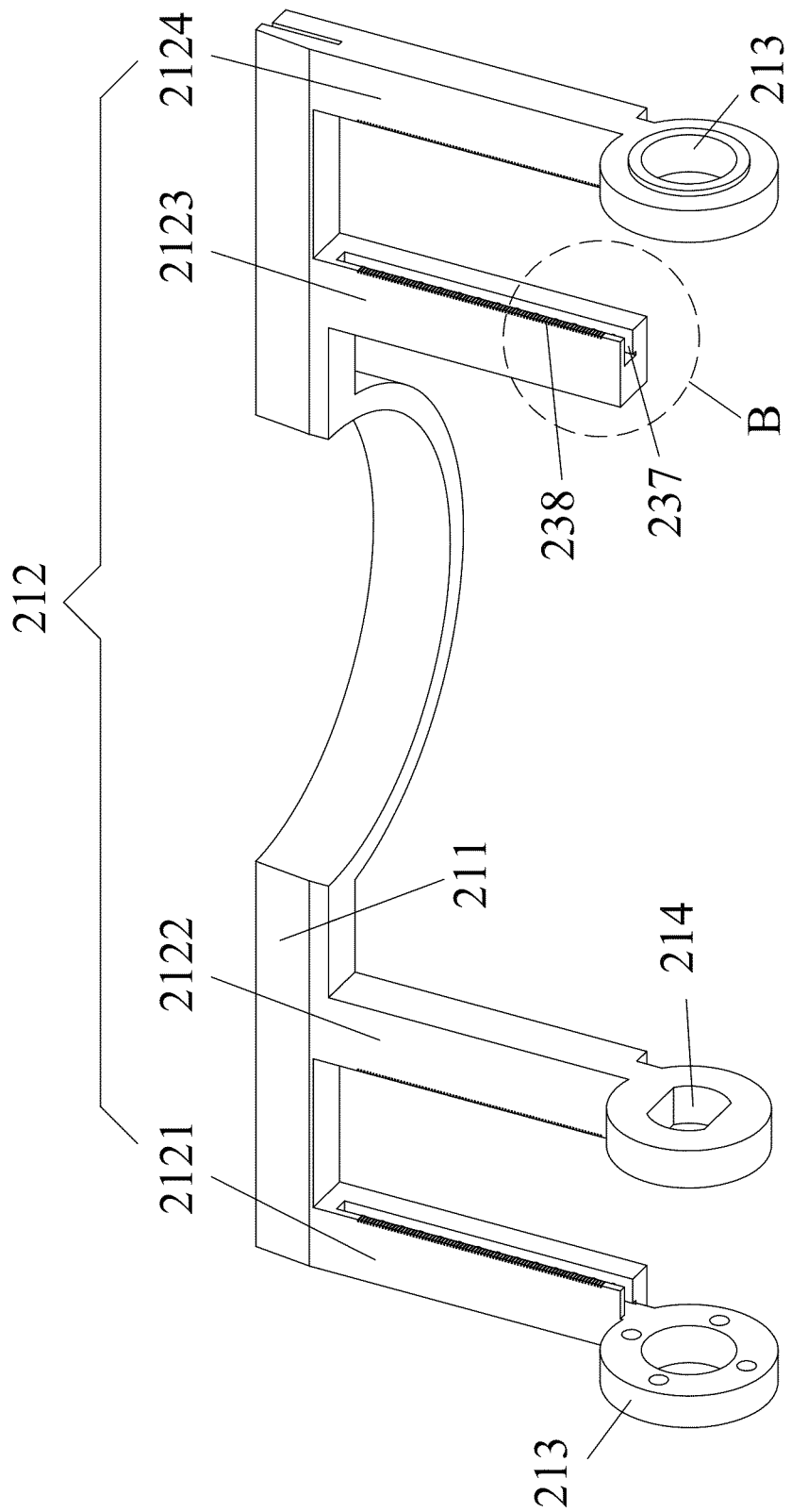
FIG. 9A is a schematic diagram of an upper folding member of one embodiment of the disclosure.
Figure 9B:
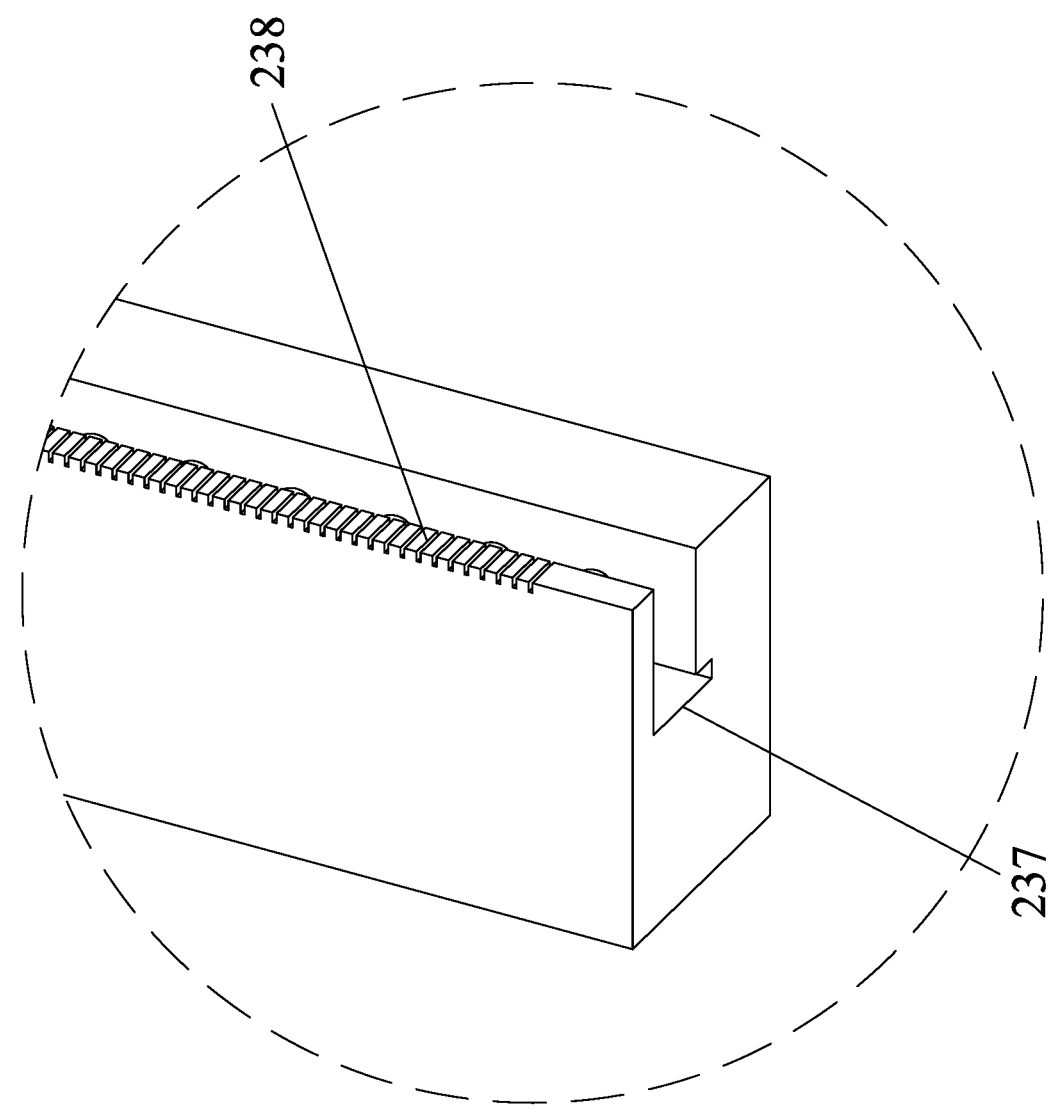
FIG. 9B is a local enlarged view of part B in FIG. 9A.
Figure 9C:
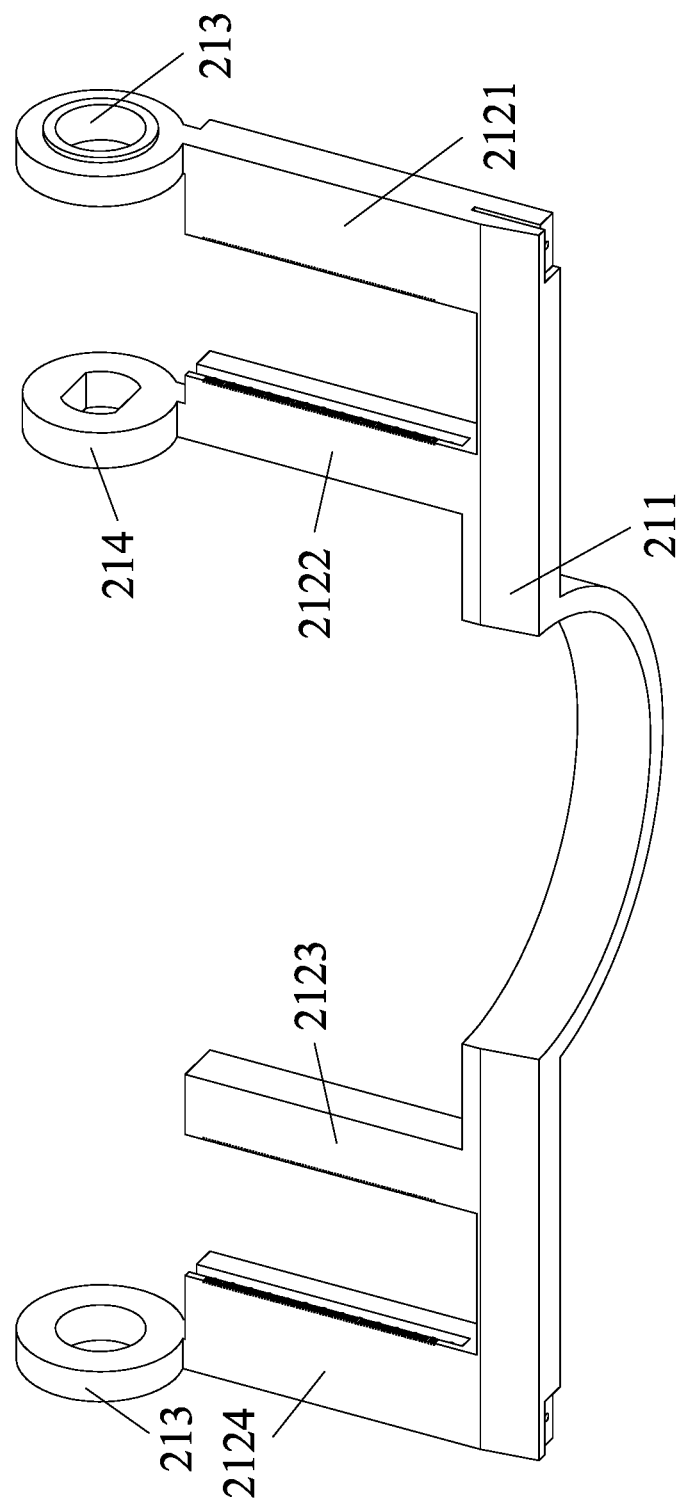
FIG. 9C is a schematic diagram of a lower folding member of one embodiment of the disclosure.
Figure 10:
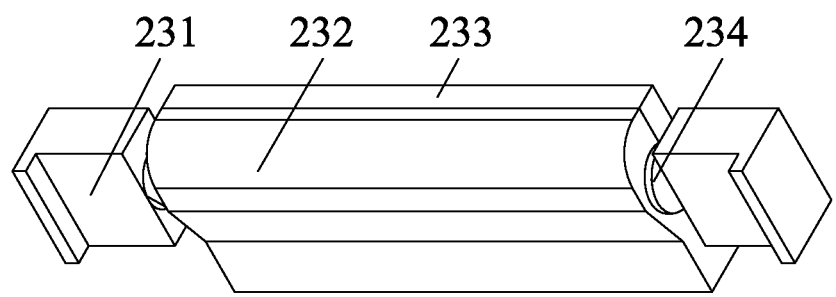
FIG. 10 is a schematic diagram of a first clamping member of one embodiment of the disclosure.
Figure 11A:
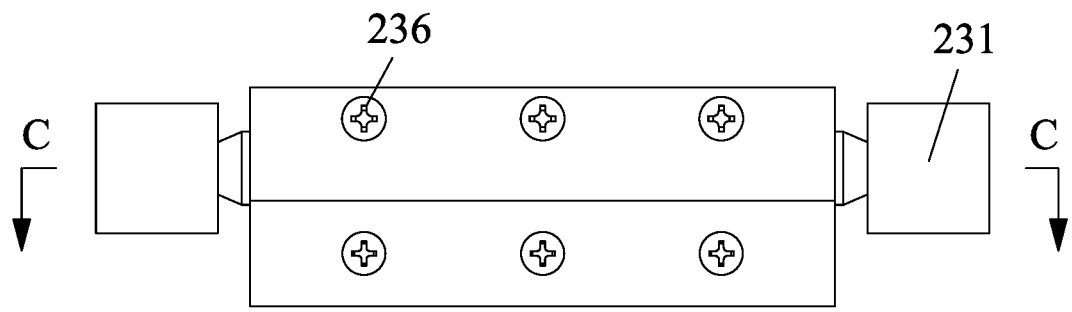
FIG. 11A is a schematic diagram of a front view of a first clamping member of one embodiment of the disclosure.
Figure 11B:
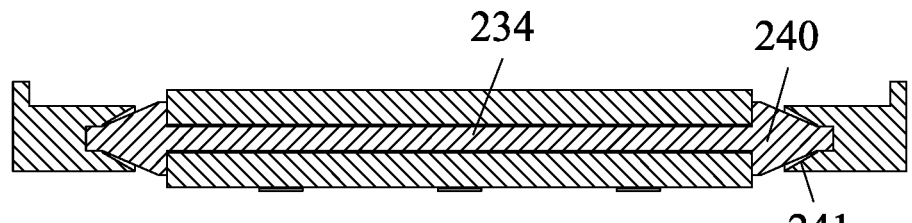
FIG. 11B is a sectional view taken from line B-B of a first clamping member in FIG. 11A.
Figure 11C:
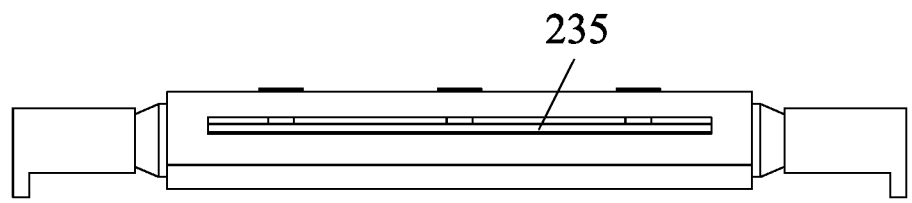
FIG. 11C is a bottom view of a first clamping member of one embodiment of the disclosure.
Figure 12A:
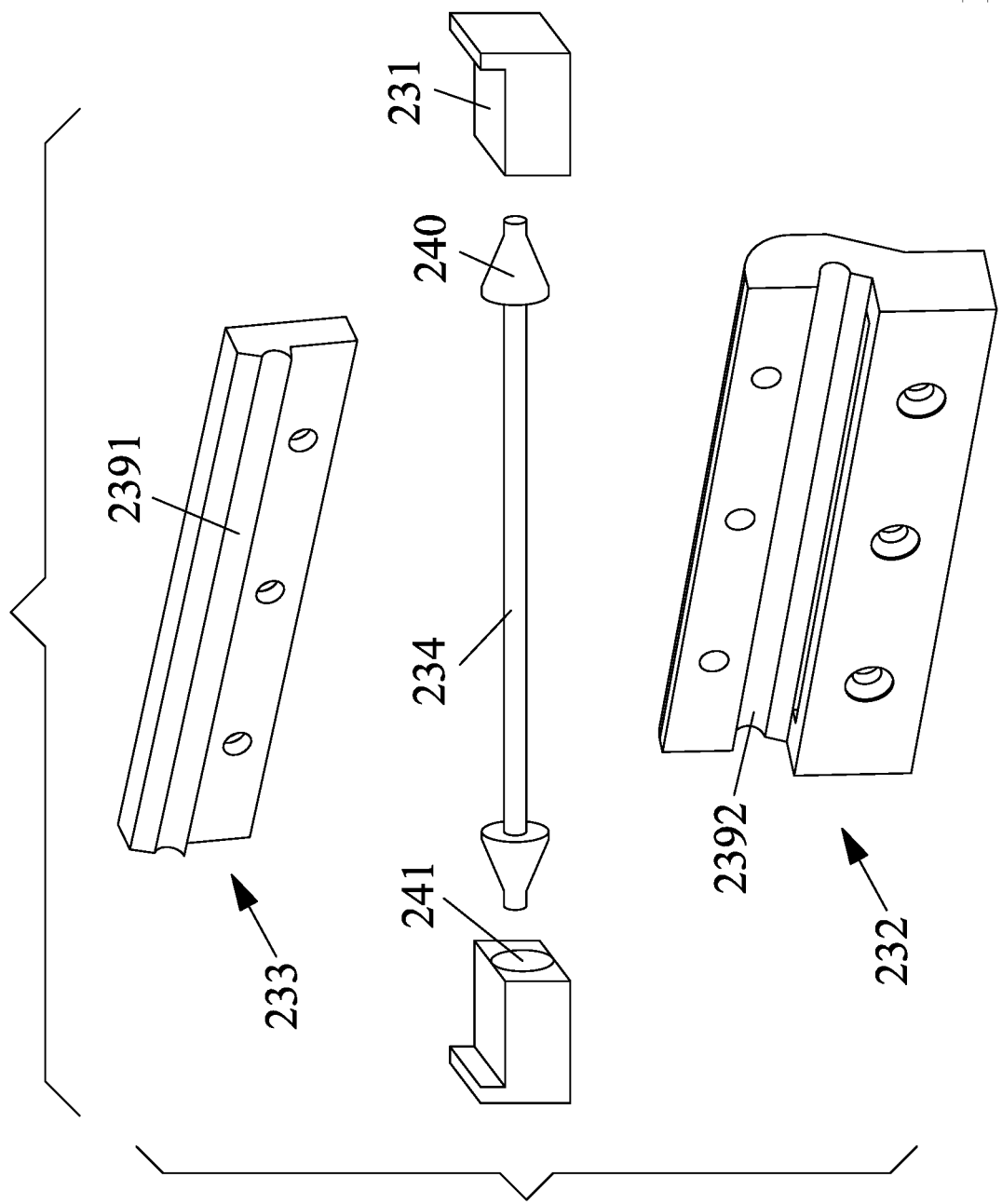
FIG. 12A is an exploded view of a first clamping member of one embodiment of the disclosure.
Figure 12C:
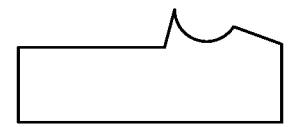
FIG. 12C is a side view of an upper clamping plate of one embodiment of the disclosure.
Figure 12B:
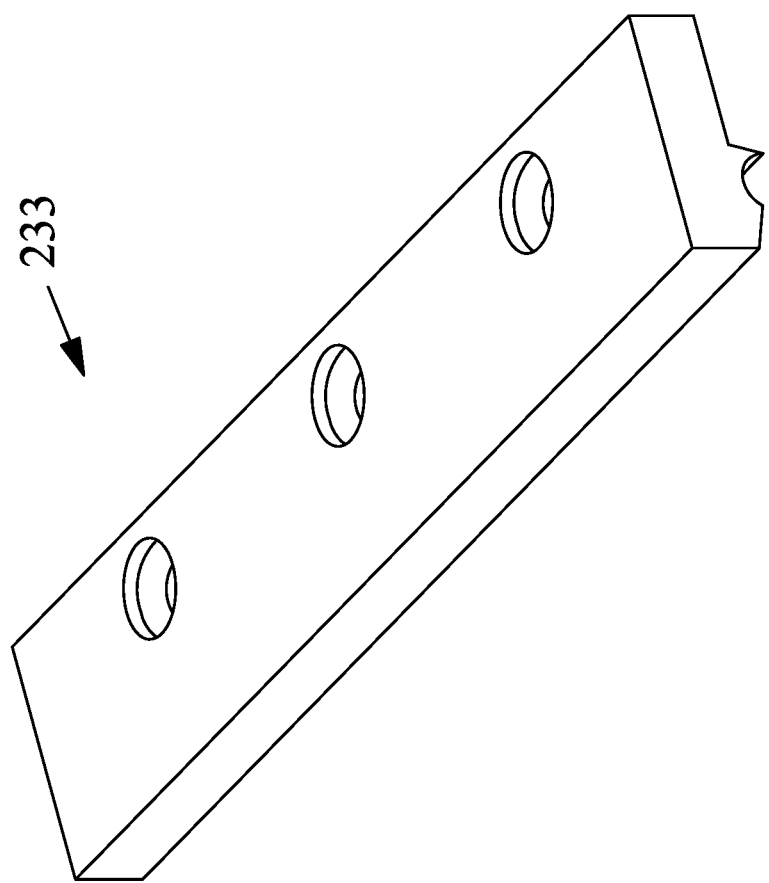
FIG. 12B is a schematic diagram of an upper clamping plate of one embodiment of the disclosure.
Figure 12E:
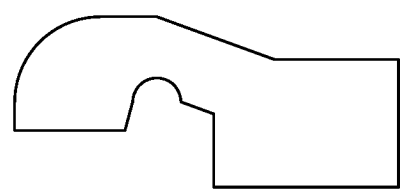
FIG. 12E is a side view of a lower clamping plate of one embodiment of the disclosure.
Figure 12D:
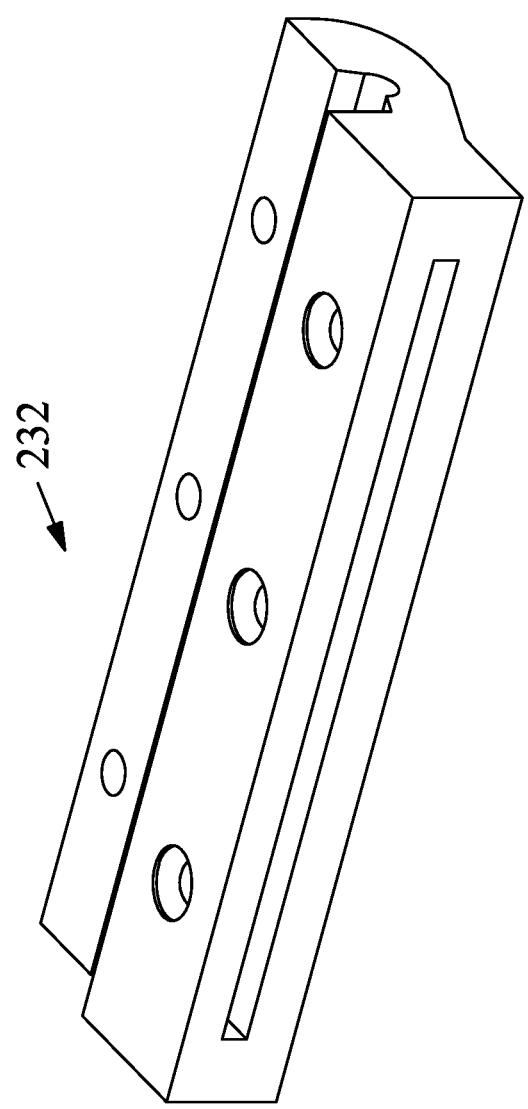
FIG. 12D is a schematic diagram of a lower clamping plate of one embodiment of the disclosure.
Figure 13B:
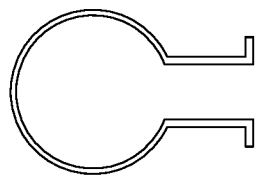
FIG. 13B is a cross sectional view of a first adjusting ring of one embodiment of the disclosure.
Figure 13A:
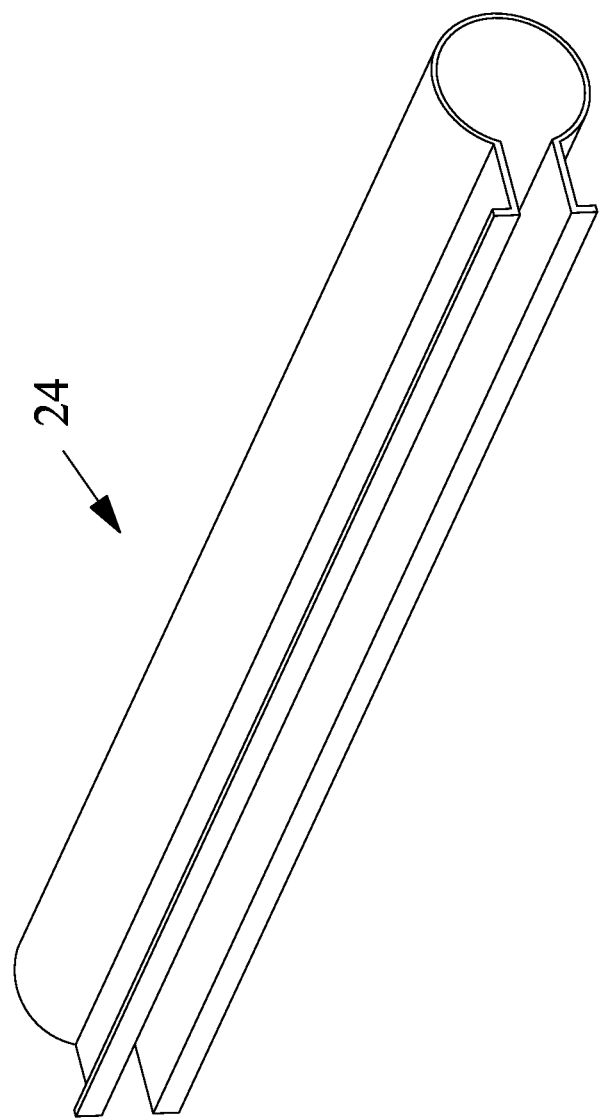
FIG. 13A is a schematic diagram of a first adjusting ring of one embodiment of the disclosure.
Figure 14:
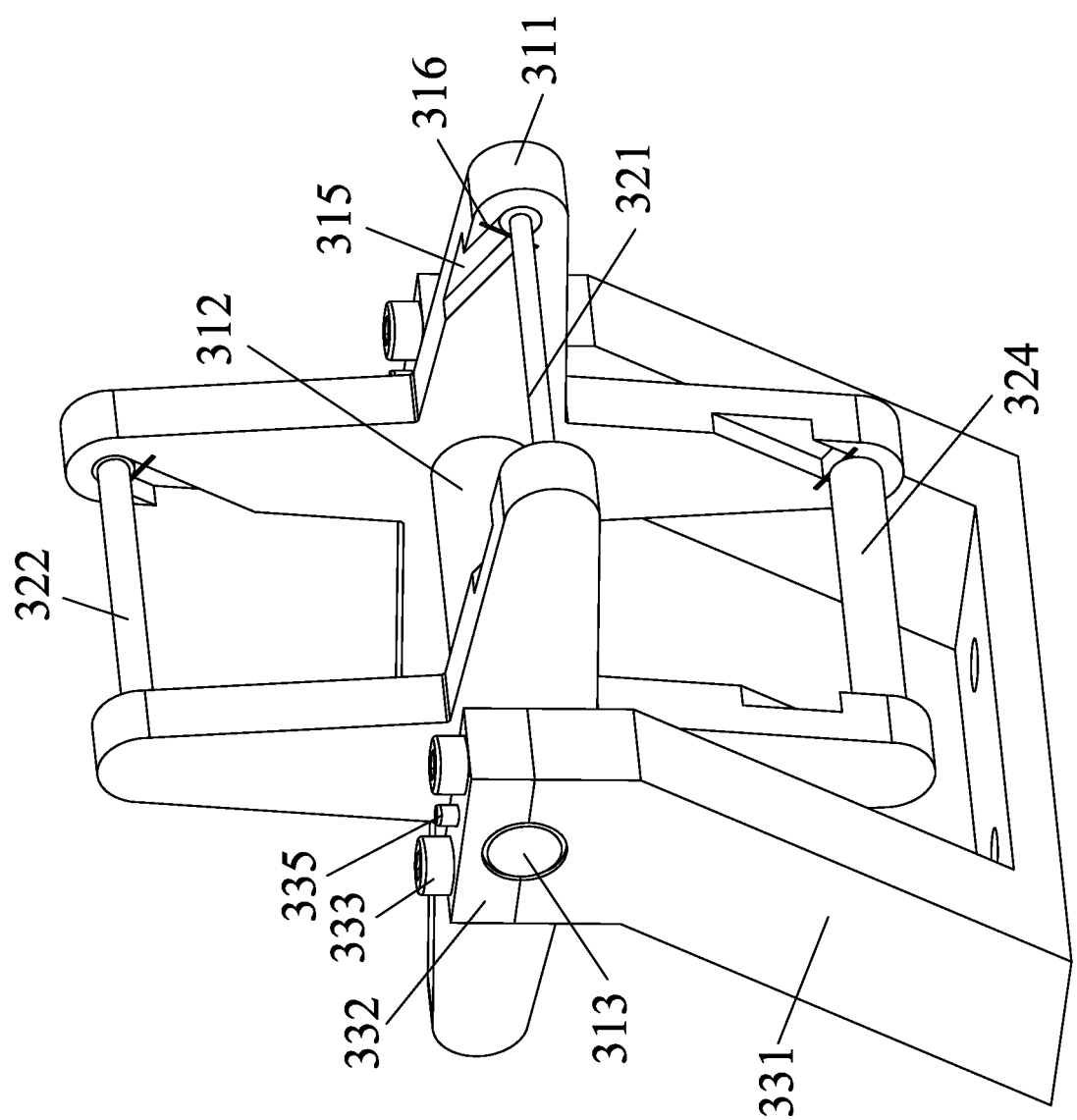
FIG. 14 is a schematic diagram of a first diameter adjustment module of one embodiment of the disclosure.
Figure 15:
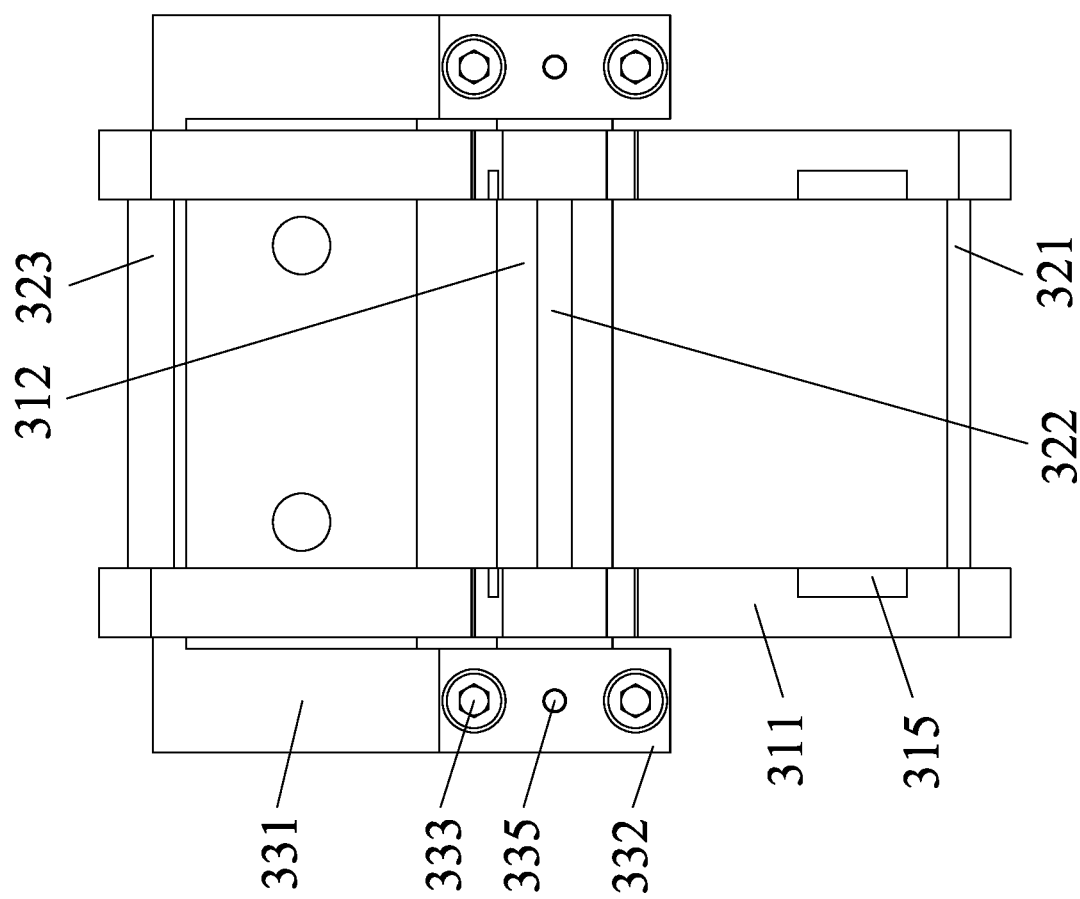
FIG. 15 is a bottom view of a first diameter adjustment module of one embodiment of the disclosure.
Figure 16:
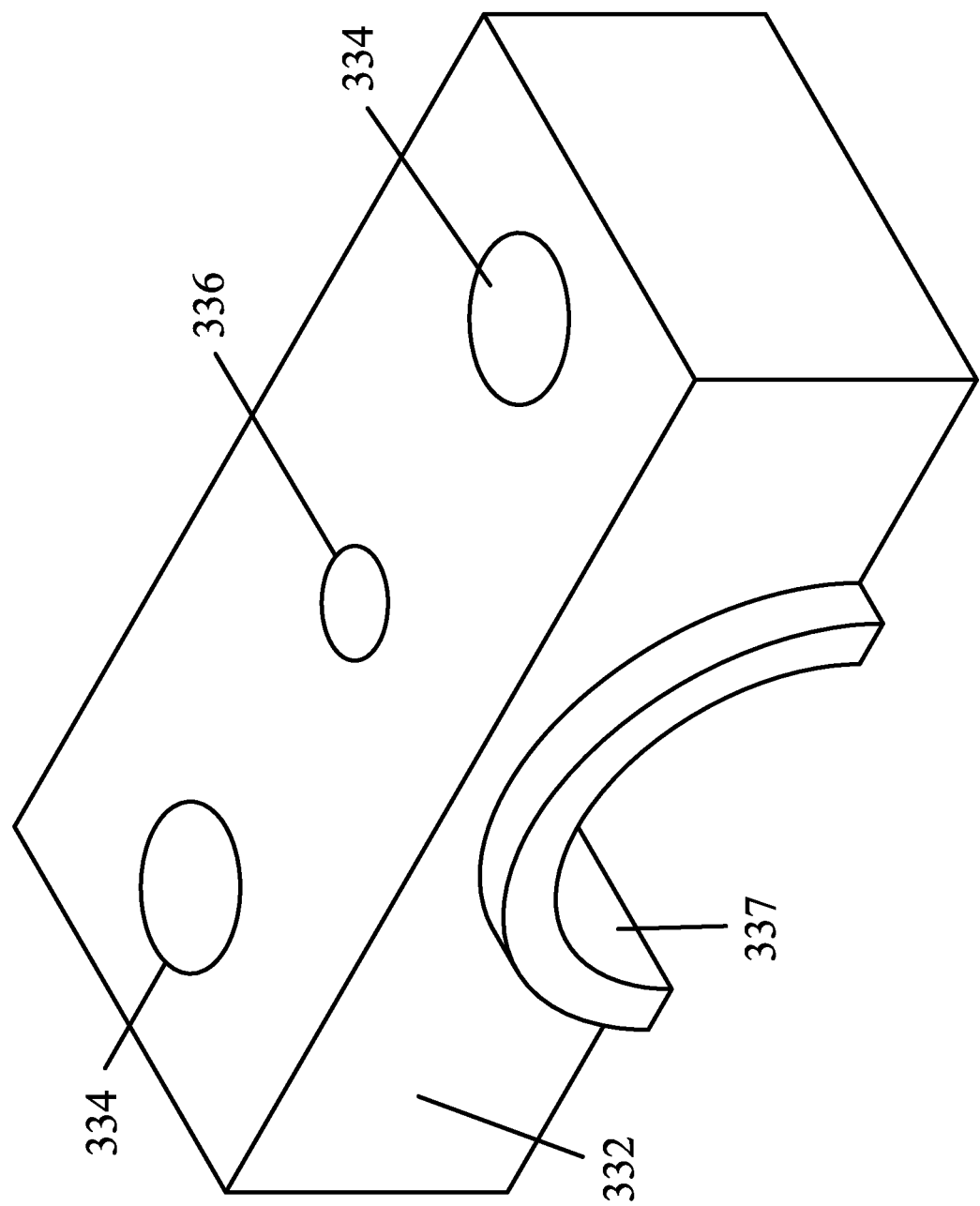
FIG. 16 is a schematic diagram of an end cover of one embodiment of the disclosure.
Figure 17:
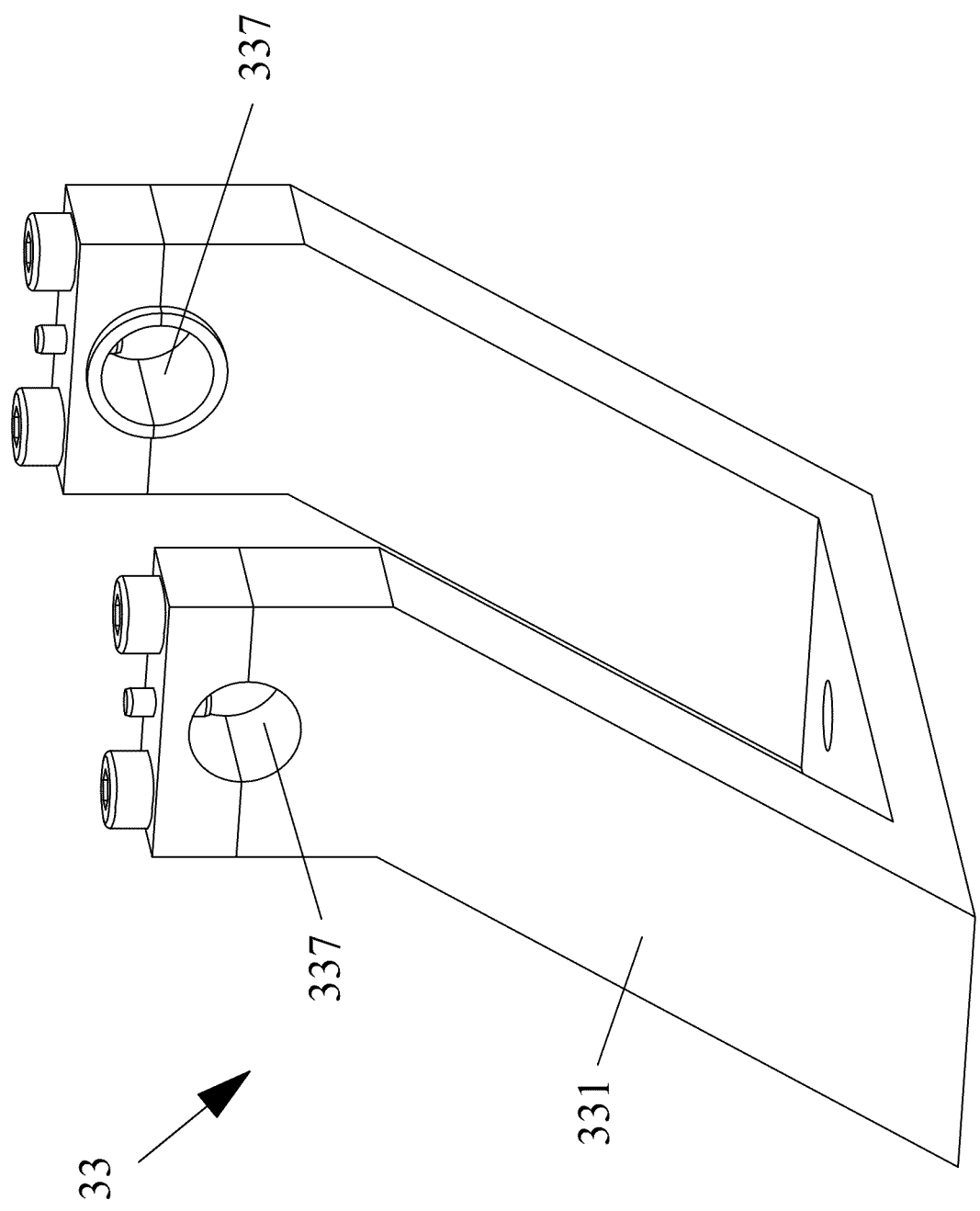
FIG. 17 is a schematic diagram of a U-shaped base of one embodiment of the disclosure.
Figure 18:
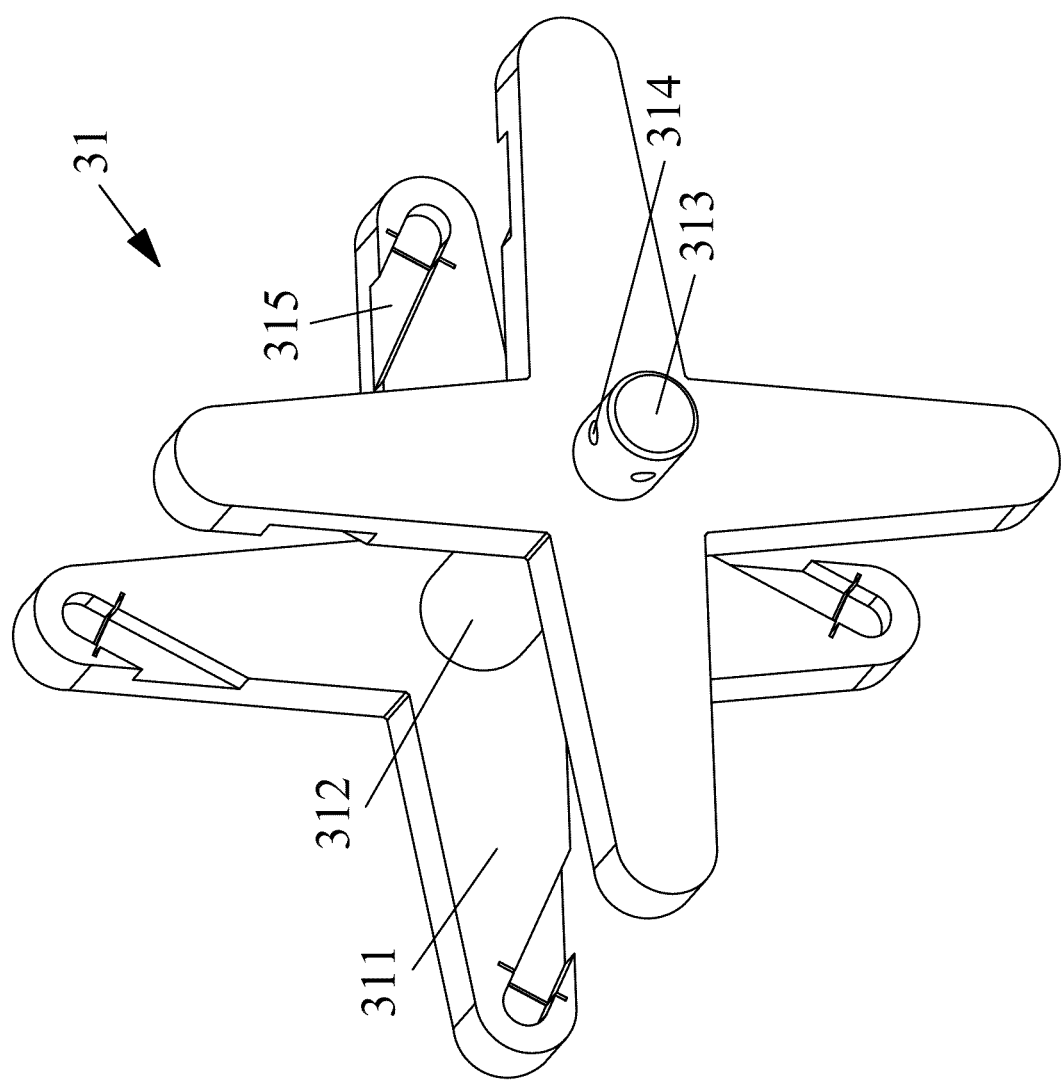
FIG. 18 is a schematic diagram of an adjustment plate of one embodiment of the disclosure.
Figure 19A:
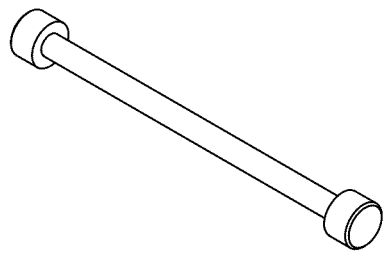
FIGS. 19A-19B are schematic diagrams of a first folding bar of one embodiment of the disclosure in different angles of view.
Figure 19B:
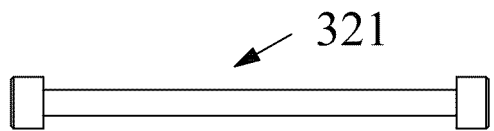
Figure 19C:
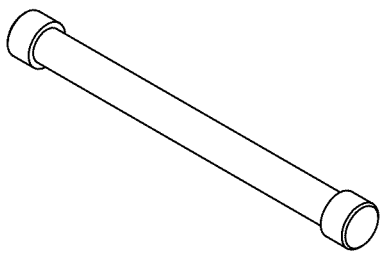
FIGS. 19C-19D are schematic diagrams of a first folding bar of one embodiment of the disclosure in different angles of view.
Figure 19D:
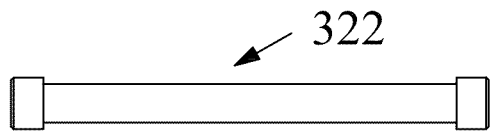
Figure 19E:
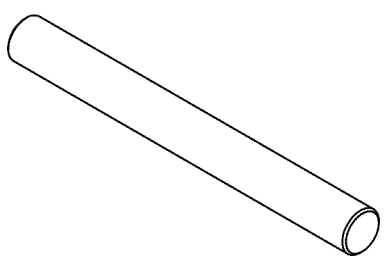
FIGS. 19E-19F are schematic diagrams of a first folding bar of one embodiment of the disclosure in different angles of view.
Figure 19F:
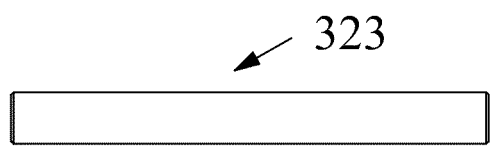
Figure 19G:
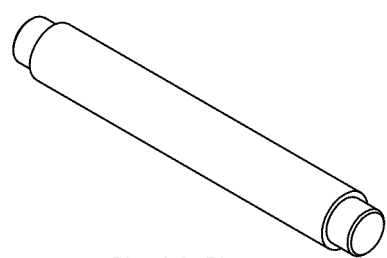
FIGS. 19G-19H are schematic diagrams of a first folding bar of one embodiment of the disclosure in different angles of view.
Figure 19H:
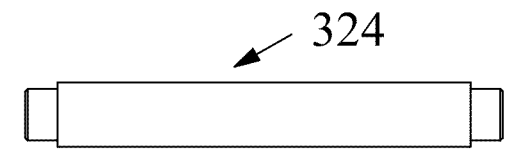
Figure 20A:
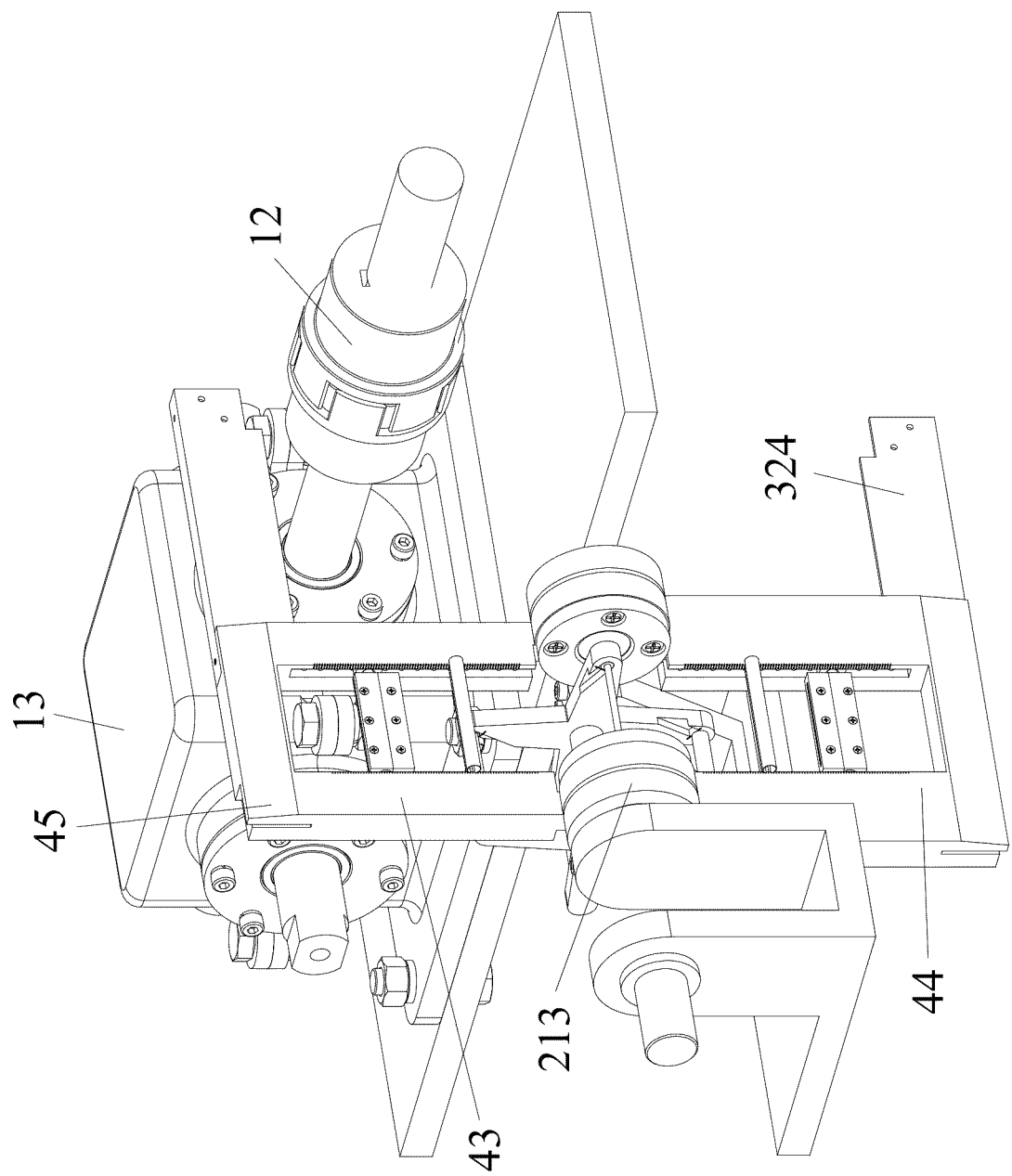
FIGS. 20A-20B are schematic diagrams of an expansion module of one embodiment of the disclosure in different angles of views.
Figure 20B:
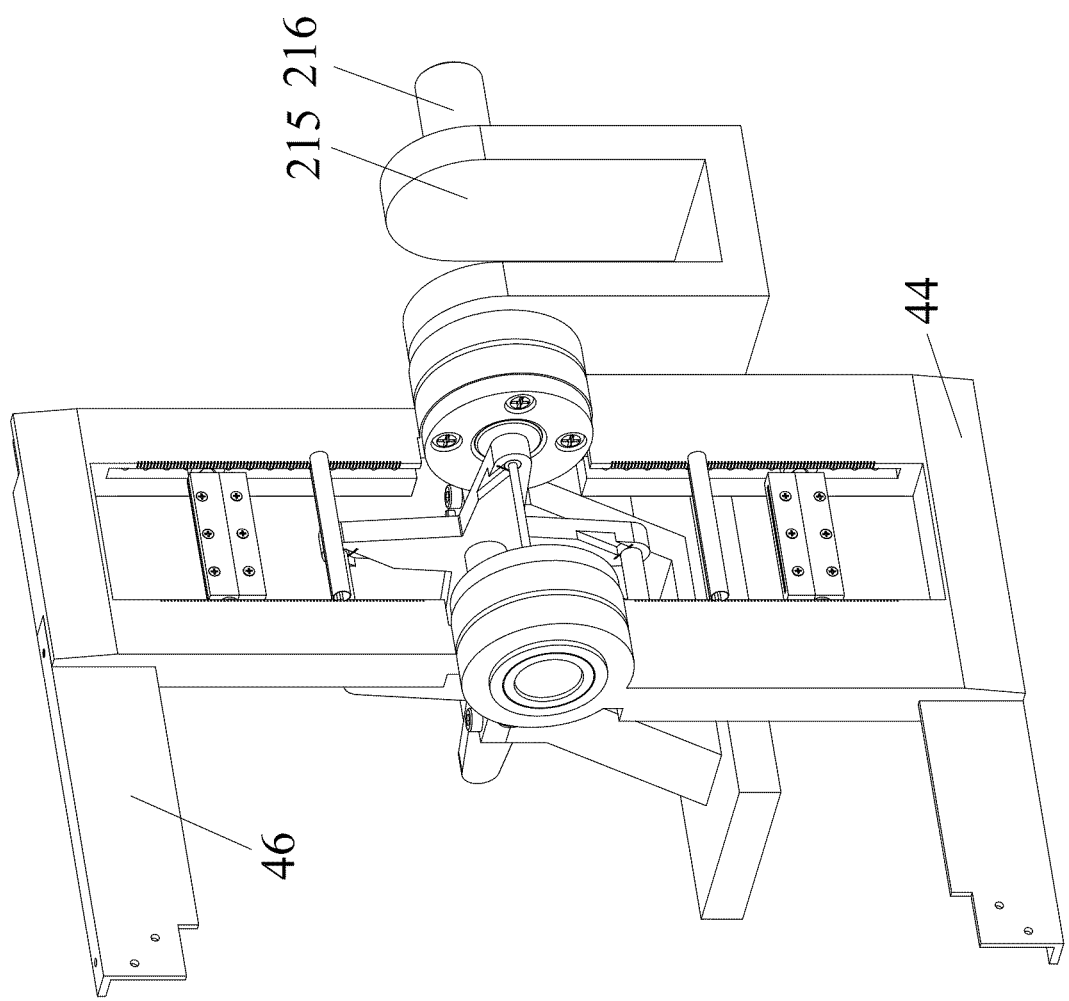
Figure 21:
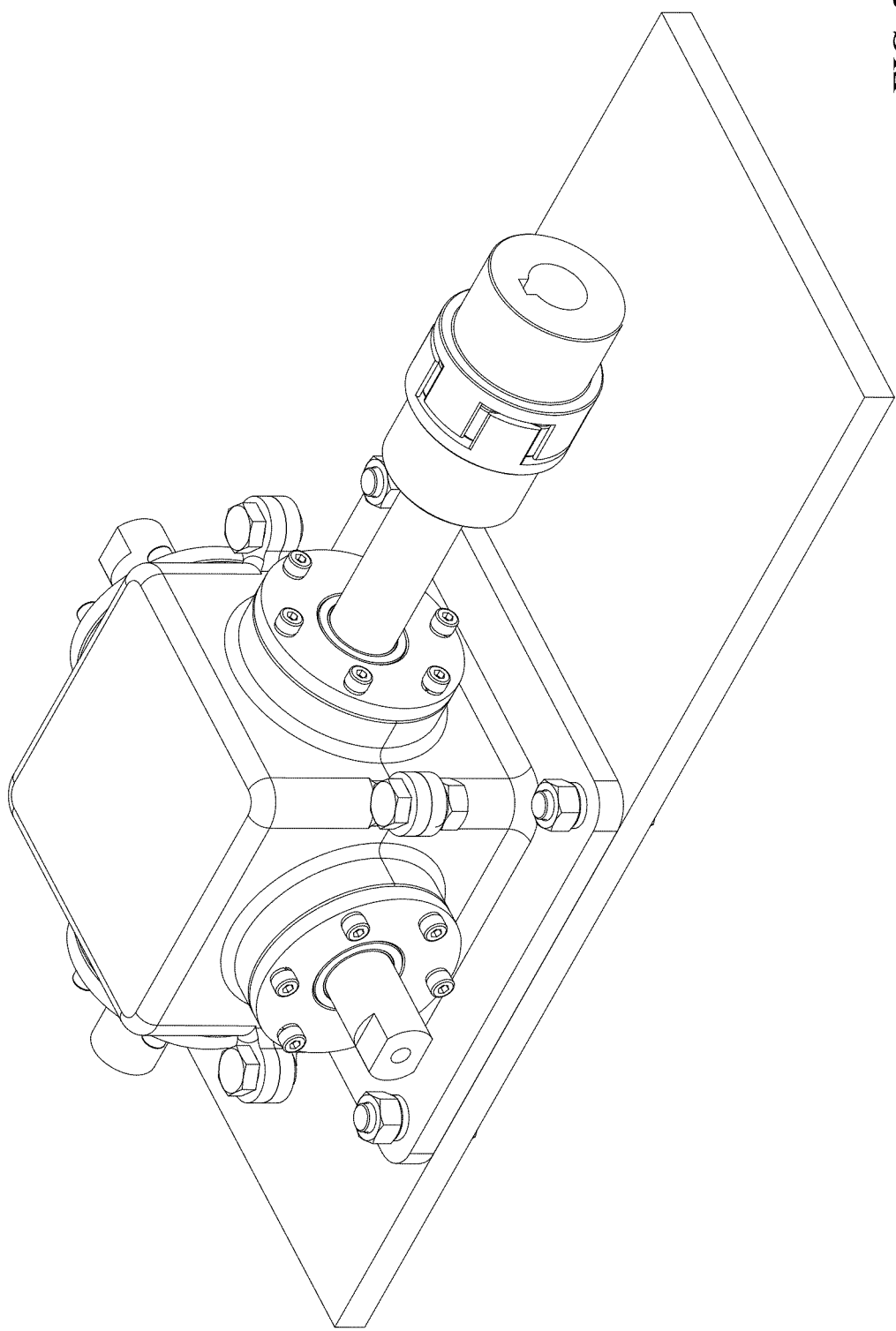
FIG. 21 is a schematic diagram of a gearbox of one embodiment of the disclosure.
Figure 22A:
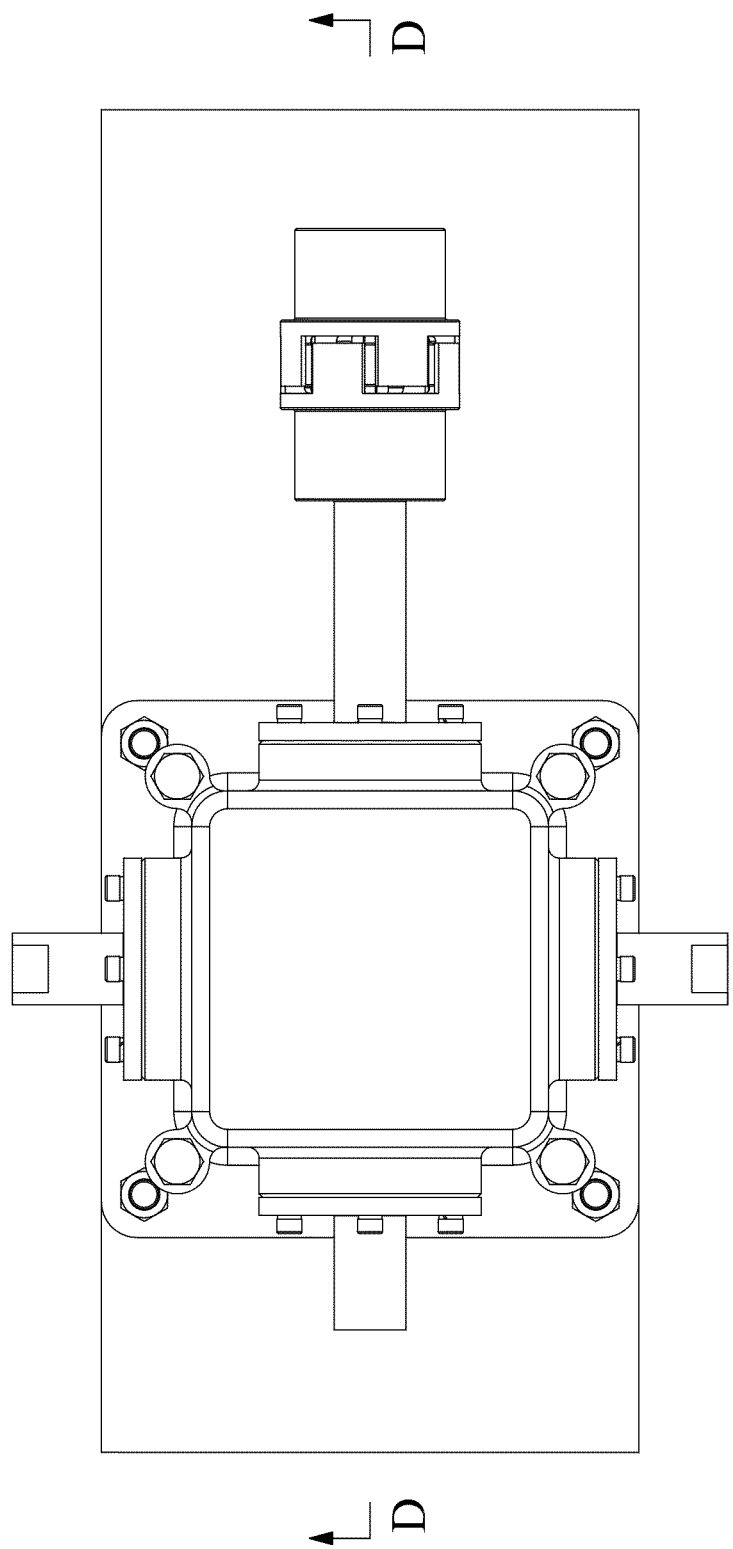
FIG. 22A is a top view of a gearbox of one embodiment of the disclosure.
Figure 22B:
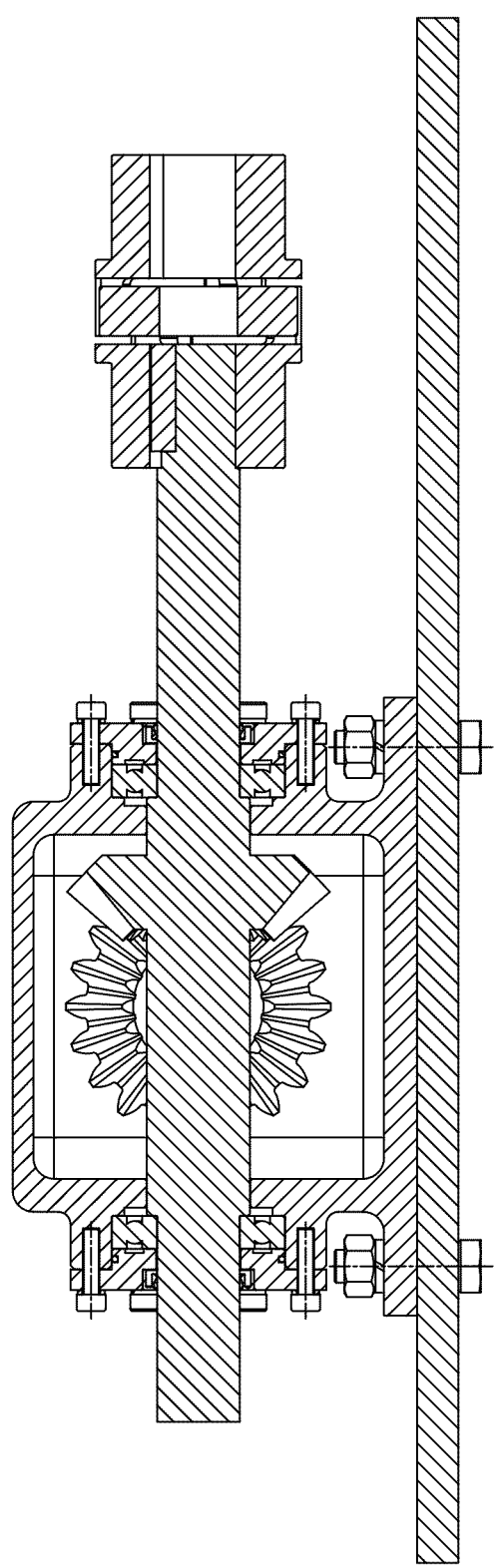
FIG. 22B is a sectional view taken from line D-D in FIG. 22A.
Figure 23B:
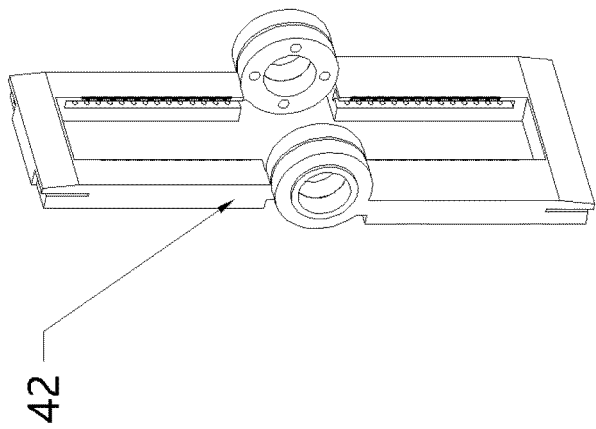
FIG. 23B is a schematic diagram of a lower expansion part of one embodiment of the disclosure.
Figure 23A:
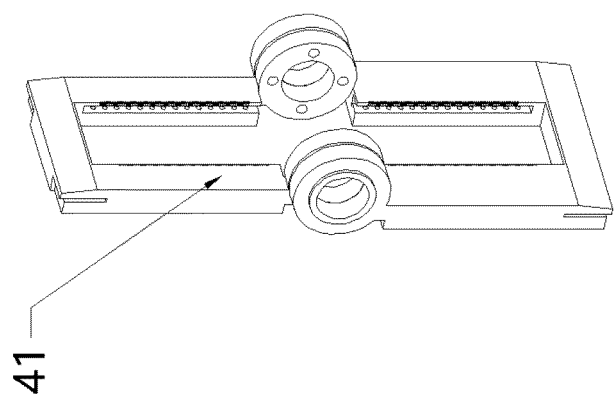
FIG. 23A is a schematic diagram of an upper expansion part of one embodiment of the disclosure.
Figure 24:
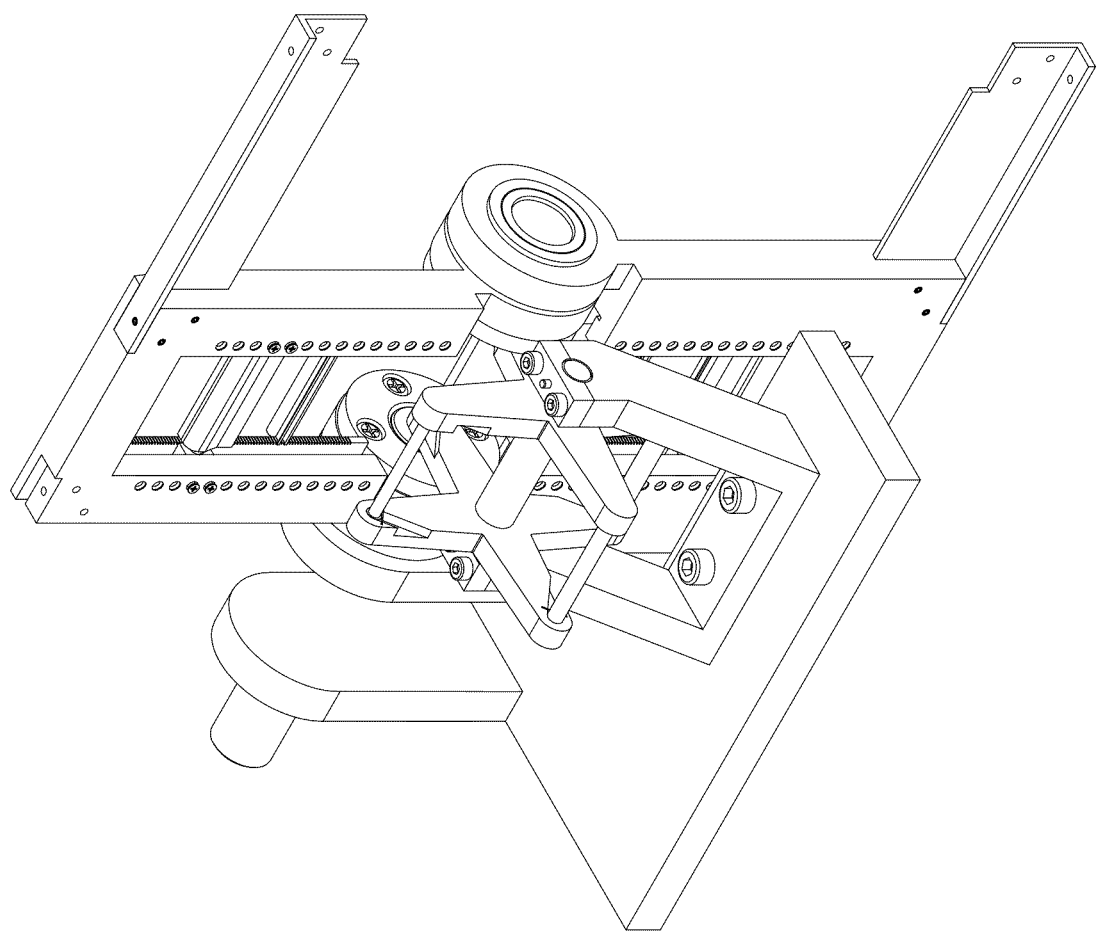
FIG. 24 is a position relationship diagram of an expansion member and a diameter adjustment module of one embodiment of the disclosure.
Figure 26:
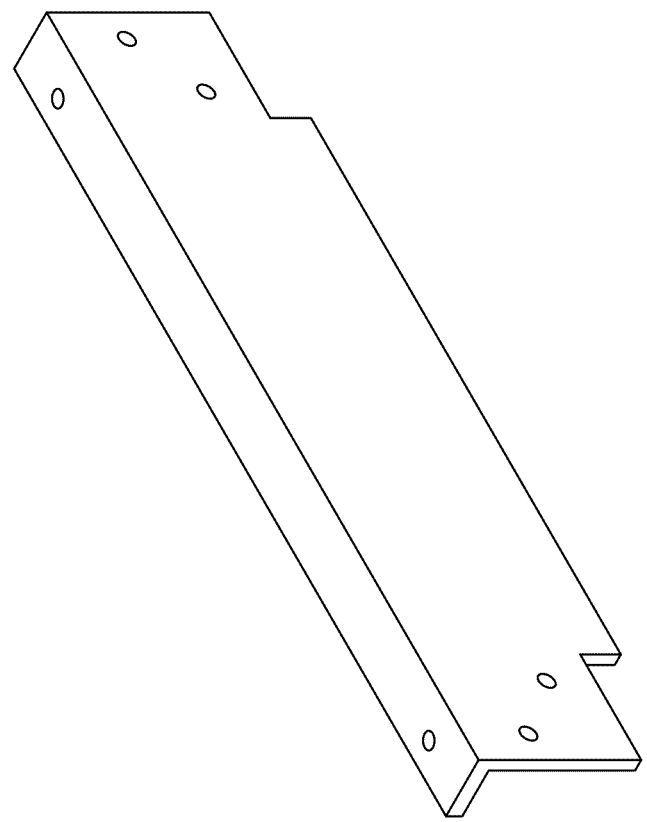
FIG. 26 is a schematic diagram of a connection plate of one embodiment of the disclosure.
Figure 25:
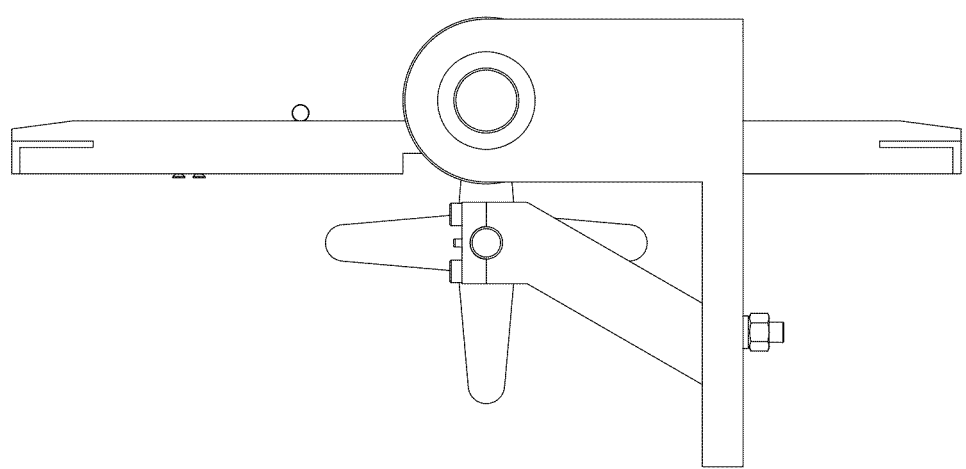
FIG. 25 is a side view of an expansion member and a diameter adjustment module of one embodiment of the disclosure.
Figure 27B:
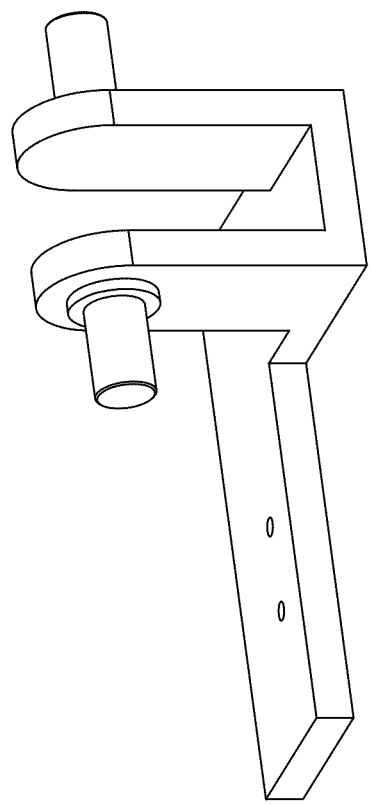
FIGS. 27A-27B are schematic diagrams of a fixing shaft of one embodiment of the disclosure in different angles of view.
Figure 27A:
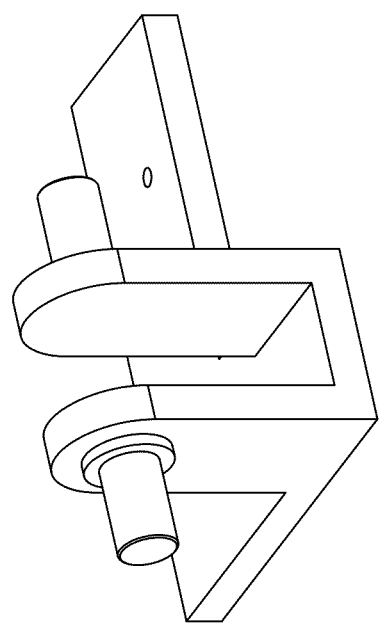
Figure 28:
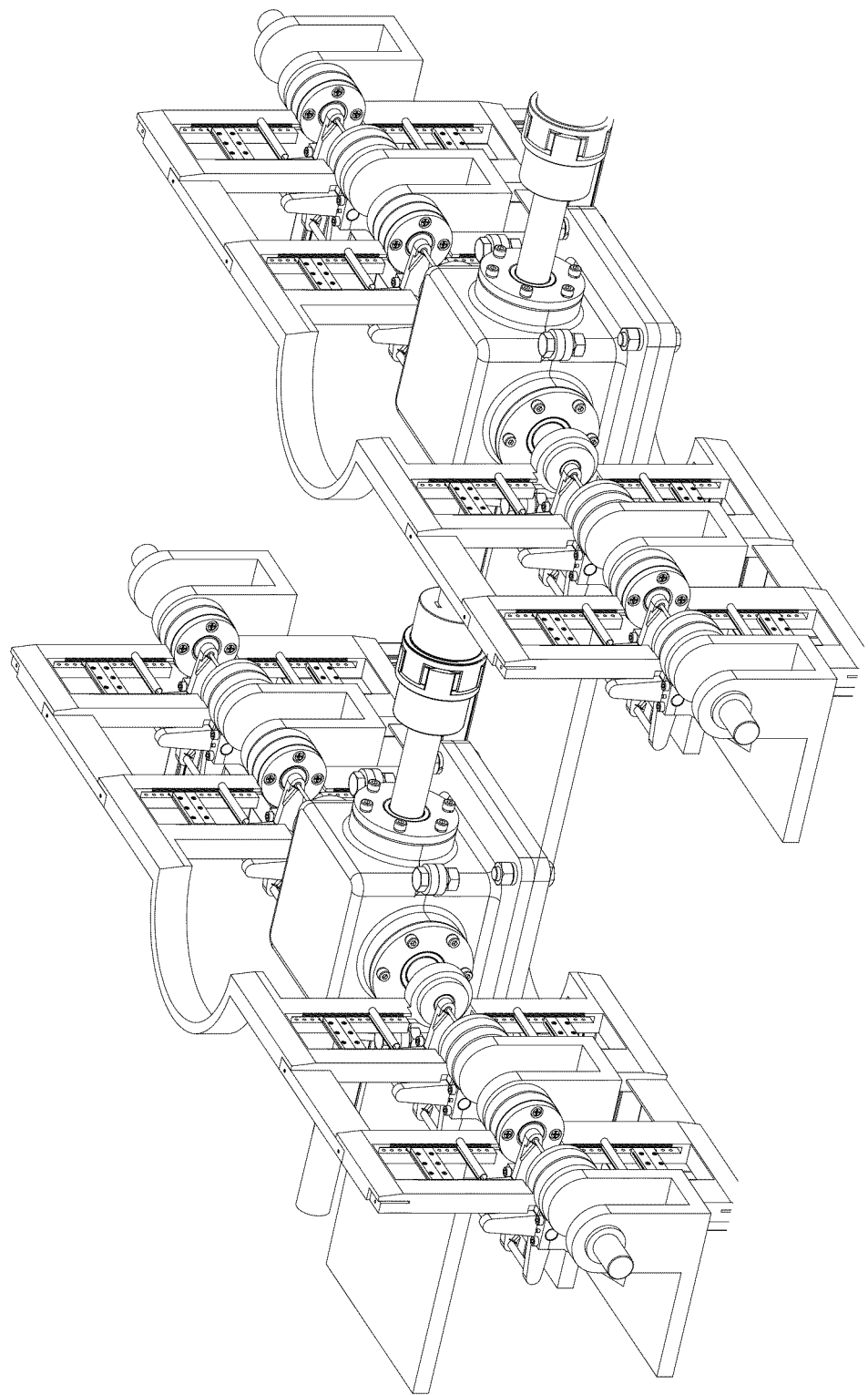
FIG. 28 is a schematic diagram of an expansion module being extended of one embodiment of the disclosure.

As shown in FIGS. 1-28, the disclosure provides a fatigue bending and folding test device for an ultra-thin metal strip. The device comprises a first driver module 1, a first folding module 2, a first diameter adjustment module 3, an expansion module 4, and a frame 5.

The first driver module 1 comprises a servo motor 11, a coupler 12, and a drive gearbox 13; the drive gearbox 13 comprises a driving gear shaft 131, a driven gear shaft 132, a plurality of output end covers 133, and a plurality of bearings 134; the drive gearbox 13 is a hollow cubic structure comprising four sidewalls with holes, and the driving gear shaft 131 and the driven gear shaft 132 are disposed through the holes; the bearings 134 are respectively disposed in the holes, and the output end covers 133 are respectively disposed outside the holes; the bearings 134 are configured to reduce friction between the drive/driven gear shaft and the drive gearbox 13, and the output end covers 133 are fixedly connected to the bearing 134, respectively; the driving gear shaft 131 is one in number and long, and the driven gear shaft 132 is two in number and short; two ends of the driving gear shaft 131 pass through two holes of the drive gearbox 13, respectively; two short driven gear shafts 132 are vertically arranged on both sides of the driving gear shaft 131 and pass through other two holes of the drive gearbox 13, respectively; the servo motor 11 is in transmission connection to one end of the driving gear shaft 131 of the drive gearbox 13 through the coupler 12; the coupler 12 is connected to the driving gear shaft 131, and the driving gear shaft 131 and the coupler 12 rotate together through keys and keyways, reducing relative sliding; the driving gear shaft 131 is equipped with a driving bevel gear 1311, and the driven gear shaft 132 is equipped with a driven bevel gear 1321; the driven gear shaft 132 is driven by the driving gear shaft 131 through gear meshing of the driving bevel gear 1311 and the driven bevel gear 1321;

the first folding module 2 comprises an upper folding member 21, a lower folding member 22, and a first mounting base 215; both the upper folding member 21 and the lower folding member 22 comprise a first crossbeam 211, a longitudinal arm 212, a first fixing ring 213, a connecting ring 214, a first clamping member 23, a first adjusting ring 24, a fixed pressure cover 25, and a first flange type self-lubricating bearing 26; the longitudinal arm 212 is four in number and four longitudinal arms 212 are perpendicularly disposed on a bottom end of the first crossbeam 211; the four longitudinal arms 212 comprises a first outer arm 2121, a first inner arm 2122, a second inner arm 2123, and a second outer arm 2124 in turn from one end to another end of the first crossbeam; the first fixing ring 213 is fixedly disposed on lower ends of the first outer arm 2121 and the second outer arm 2124 of the upper folding member 21; the connecting ring 214 is disposed on a lower end of the first inner arm 2122 on the upper folding member 21; the first fixing ring 213 is fixedly disposed on lower ends of the first outer arm 2121 and the second outer arm 2124 of the lower folding member 22; the connecting ring 214 is disposed on a lower end of the first inner arm 2122 of the lower folding member 22; the first crossbeam 211 of the lower folding member 22 is wider than the first crossbeam 211 of the upper folding member 21, so that two first fixing rings 213 of the lower folding member 22 are disposed outside two first fixing rings 213 of the upper folding member 21; the two first fixing rings 213 of the upper folding member 21 and the two first fixing rings 213 of the lower folding member 22 overlap with each other through the rotation of the lower folding member 22, and the first flange type self-lubricating bearing 26 is attached to an inner side of each of the two first fixing rings 213 of the upper folding member 21; a threaded hole is disposed on an inner side of each of the two first fixing rings 213 of the upper folding member 21, and the first flange type self-lubricating bearing 26 is fixed in the threaded hole by screws; a first side of the connecting ring 214 of the upper folding member and the lower folding member, facing the second inner arm 2123, comprises a square hole to receive the driven gear shaft 132, thereby limiting a radial rotation of the upper folding member 21 and the lower folding member 22, so that the upper folding member 21 and the lower folding member 22 is only rotatable with one of the two driven gear shafts 132; the driven output shafts 132 rotate to fold the upper folding member 21 and lower folding member 22 inward; the fixed pressure cover 25 is disposed on a second side of the connecting ring 214 of the upper folding member and the lower folding member; the fixed pressure cover 25, the driven output shaft 132, and the connecting ring 214 are fixed together through fixing screws thus preventing an axial movement of the upper folding member 21 and the lower folding member 22; the first mounting base 215 comprises two first fixing shafts 216 which are mutually symmetrical, and the two first fixing shafts 216 extends outside the first fixing ring 213 for installing folding members; the inner sides of the first outer arm 2121 and the first inner arm 2122 and inner sides of the second outer arm 2123 and the second inner arm 2124 of the upper folding member 21 and the lower folding member 22 are all provided with clamping grooves 238 and L-shaped sliding grooves 237; a row of fixed threaded holes are disposed on back sides of the first outer arm 2121, the first inner arm 2122, the second outer arm 2123, and the second inner arm 2124, and the back sides are adjacent to the inner sides; the first clamping member 23 comprises a sliding block 231, a lower clamping plate 232, an upper clamping plate 233, a rotating shaft 234, an intermediate pressure plate 235, and a plurality of fixing bolts 236; the upper parts of the upper clamping plate 233 and the lower clamping plate 232 comprise a plurality of threaded holes for fixed connection of the upper clamping plate 233 and the lower clamping plate 232; a lower part of the upper clamping plate 233 comprise a first shaft groove 2391 and a middle part of the lower clamping plate 232 comprise a second shaft groove 2392 for receive the rotating shaft 234; a lower part of the lower clamping plate 232 comprises a plurality of threaded holes, and a bottom part of the lower clamping plate 232 comprises a rectangular opening; the intermediate pressure plate 235 and an ultra-thin metal strip are disposed through the rectangular opening; two ends of the rotating shaft 234 comprise umbrella-shaped protrusions 240, and an inner side of the sliding block 231 comprises an umbrella-shaped groove 241 configured to cooperate with the umbrella-shaped protrusions 240 at two ends of the rotating shaft 234 to enable the rotating shaft 234 to rotate in the sliding block 231; an outer side of the sliding block 231 comprises a bulge that matches the L-shaped sliding grooves 237, so that the sliding block 231 is flexibly clamped inside the L-shaped sliding grooves 237; the first clamping member 23 is adjustable up and down between the first outer arm 2121 and the first inner arm 2122, and between the second inner arm 2123 and the second outer arm 2124 according to a size requirement of the ultra-thin metal strip to be tested; sliding blocks 231 on both sides of the first clamping member 23 are fixed by tightening screws, thereby fixing the first clamping member 23; the first adjusting ring 24 has a cross-section in the shape of an "Ω", and two ends of the first adjusting ring are respectively disposed in the clamping grooves 238; the first adjusting ring 24 is adjusted according to requirements and a folding diameter of the ultra-thin metal strip to be tested;

the intermediate pressure plate 235 covers the ultra-thin metal strip and passes through the rectangular opening at the bottom part of the lower clamping plate 232. The screws 236 pass through the threaded holes at the bottom of the lower clamping plate 232 to press the intermediate pressure plate 235, thereby pressing the ultra-thin metal strip. The rotating shaft 234 is disposed on the second shaft groove 2392 of the lower clamping plate 232, and then the first shaft groove 2391 of the upper clamping plate 233 is aligned with the opening of the second shaft groove 2392 of the lower clamping plate 232, so that the rotating shaft 234 is installed in the shaft groove. Through the fixing of the upper clamping plate 233 and the lower clamping plate 232 with the screws 236, so that the upper clamping plate 233 and the lower clamping plate 232 rotate around the rotating shaft 234.

The first diameter adjustment module 3 comprises an adjustment plate 31, a folding bar, and a support base 33; the adjustment plate 31 comprises two cross-shaped plates 311, a connecting rod 312, and a second fixing shaft 313; the connecting rod 312 is fixedly disposed on inner centers of the two cross-shaped plates 311, and the second fixing shaft 313 is fixedly disposed on outer centers of the two cross-shaped plates 311; the connecting rod 312 and the second fixing shaft 313 are coaxial; an inner side of each of four top ends of each of the two cross-shaped plates 311 comprises a chute 315 for receiving the folding bar; a limiting plate 316 is movably disposed in the chute 315 to fix the folding bar on a corresponding top end of each of the two cross-shaped plates 311; the second fixing shaft 313 comprises two locking through holes 314 perpendicular to each other to form a "+" shape, corresponding to the four top ends of each of the cross-shaped plates 311; the folding bar are four in number with different diameters, and comprises a first folding bar 321, a second folding bar 322, a third folding bar 323, and a fourth folding bar 324;

the support base 33 comprises a U-shaped base 331 and two end covers 332; two top ends of the U-shaped base 331 comprises two first mounting grooves 337, respectively, and the second fixing shaft 313 is disposed in the two first mounting grooves; a lower part of each of the two end covers 332 comprises a second mounting grooves, and two second mounting grooves correspond to the two first mounting grooves, respectively; a top part of each of the two end covers 332 comprises two tap holes 334 and a locking pin hole 336 with the same diameter as the locking through holes 314 for receiving a locking pin 335; the two end covers 332 are fixed on the U-shaped base 331 through tightening screws 333; the locking pin 335 passes through the locking pin hole 336 and enters one of the locking through holes 314 of the second fixing shaft 313 to prevent a radial rotation of the adjustment plate 31;

the expansion module 4 comprises a second driver module without a servo motor, a second folding module, a second diameter adjustment module, a first expansion member 41 and a second expansion member 42; the second driver module without a servo motor is in transmission connection to another end of the driving gear shaft 131 of the drive gearbox 13 through the coupler 12, so that a power of the expansion module 4 is output forward; the first expansion member 41 and the second expansion member 42 each comprise an upper expansion part 43 and a lower expansion part 44; the upper expansion part 43 and the lower expansion part 44 each comprise a second crossbeam 45, a third outer arm, a fourth outer arm, and a second fixing ring; the second fixing ring is fixedly disposed on lower ends of the third outer arm and the fourth outer arm; the second crossbeam of the lower expansion part is wider than the second crossbeam of the upper expansion part, so that two second fixing rings of the lower expansion part are disposed outside two second fixing rings of the upper expansion part; the two second fixing rings of the upper expansion part 43 and the two second fixing rings of the lower expansion part 44 overlap with each other, and a second flange type self-lubricating bearing is attached to an inner side of the two second fixing rings of the third outer arm and the fourth outer arm of the upper expansion part 43; a threaded hole is disposed on an inner side of each of the two second fixing rings of the upper expansion part 43, and the second flange type self-lubricating bearing is fixed in the threaded hole by screws; a second mounting base is disposed on an outer side of each of the two second fixing rings to fix the first expansion member and the second expansion member; the expansion module 4 further comprises a second clamping member and a second adjusting ring which are disposed the same as that in the first folding module; the first expansion member 41 and the second expansion member 42 are respectively disposed on two sides of the first folding module 2, and are respectively fixed on corresponding second mounting bases; the upper expansion part 43 is connected to the upper folding member 21 through a first connection plate 46, and the lower expansion part 44 is connected to the lower folding member 22 through a second connection plate 46, so that the upper expansion part 43 and the upper folding member 21 of the first folding module 2 rotate coaxially, and the lower expansion part 44 and the lower folding member 22 of the first folding module 2 rotate coaxially, thereby achieving expansion and extension of the first folding module 2 in two directions.

When it is necessary to replace the folding bar, the locking pin 335 is directly pulled out, the adjustment plate 31 is rotated, or directly pulling out the limiting plate 316 to replace the folding bar.

The cooperation of the first adjusting ring 24 with the first clamping member 23 enables the tested ultra-thin metal strip to adhere to the first folding bar 321 of the first diameter adjustment module 3, facilitating the implementation of fatigue bending and folding tests of the ultra-thin metal strip.

The first diameter adjustment module 3 is disposed behind the first folding module 2, and an axis of the folding bar of the first folding module 2 is coaxial to an axis of the first flange type self-lubricating bearing 26 in the first fixing ring 213 of the first folding module 2; the first diameter adjustment module 3 is disposed between the first outer arm 2121 and the first inner arm 2122, between the second inner arm 2123 and the second outer arm 2124 of the first folding module 2, and between the third outer arm and the fourth outer arm of the first expansion member 41 and the second expansion member 42 of the expansion module 4.

The middle part of the first crossbeam 211 is arc-shaped to avoid the driving gear shaft 131 and the coupler 12.

The first connection plate 46 and the second connection plate 46 are disposed between the first crossbeam 211 and the second crossbeam 45.

A strain gauge is disposed inside the first diameter adjustment module 3 to measure stress-strain data of the ultra-thin metal strip.

The expansion module 4 is extended in multiple directions through couplers, and a number of extensions is limited by a number of samples to be tested and working parameters of the servo motor 11.

A control system of the servo motor 11 of the first driver module 1 is connected to a computer to set a folding angle and a folding speed of the ultra-thin metal strip, to complete tests under different working conditions.

The ultra-thin metal strip comprises a stainless steel ultra-thin strip, copper ultra-thin strip, titanium ultra-thin strip, or a composite ultra-thin strip.

The frame 5 is an aluminum profile frame.

A cross-section of the first and second connection plate 46 is L-shaped.

It will be obvious to those skilled in the art that changes and modifications may be made, and therefore, the aim in the appended claims is to cover all such changes and modifications.

What is claimed is:

1. A fatigue bending and folding test device for an ultra-thin metal strip, the device comprising:
   a first driver module;
   a first folding module;
   a first diameter adjustment module;
   an expansion module; and
   a frame;
   wherein:
   the first driver module, the first folding module, the first diameter adjustment module, and the expansion module are all disposed on the frame;

the first driver module comprises a servo motor, a coupler, and a drive gearbox; the drive gearbox comprises a driving gear shaft, a driven gear shaft, a plurality of output end covers, and a plurality of bearings; the drive gearbox is a hollow cubic structure comprising four sidewalls with holes, and the driving gear shaft and the driven gear shaft are respectively disposed through the holes; the bearings are respectively disposed in the holes, and the plurality of output end covers are respectively disposed outside the holes; the bearings are configured to reduce friction between the drive/driven gear shaft and the drive gearbox, and the output end covers are fixedly connected to the bearings, respectively; the driving gear shaft is one in number and long, and the driven gear shaft is two in number and short; two ends of the driving gear shaft pass through two holes of the drive gearbox, respectively; two short driven gear shafts are vertically arranged on both sides of the driving gear shaft and pass through other two holes of the drive gearbox, respectively; the servo motor is in transmission connection to one end of the driving gear shaft of the drive gearbox through the coupler; the coupler is connected to the driving gear shaft, and the driving gear shaft and the coupler rotate together through keys and keyways, reducing relative sliding; the driving gear shaft is equipped with a driving bevel gear, and the driven gear shaft is equipped with a driven bevel gear; the driven gear shaft is driven by the driving gear shaft through gear meshing of the driving bevel gear and the driven bevel gear;

the first folding module comprises an upper folding member, a lower folding member, and a first mounting base; both the upper folding member and the lower folding member comprise a first crossbeam, a longitudinal arm, a first fixing ring, a connecting ring, a first clamping member, a first adjusting ring, a fixed pressure cover, and a first flange type self-lubricating bearing; the longitudinal arm is four in number and four longitudinal arms are perpendicularly disposed on a bottom end of the first crossbeam; the four longitudinal arms comprises a first outer arm, a first inner arm, a second inner arm, and a second outer arm in turn from one end to another end of the first crossbeam; the first fixing ring is fixedly disposed on lower ends of the first outer arm and the second outer arm of the upper folding member; the connecting ring is disposed on a lower end of the first inner arm on the upper folding member; the first fixing ring is fixedly disposed on lower ends of the first outer arm and the second outer arm of the lower folding member; the connecting ring is disposed on a lower end of the first inner arm of the lower folding member;

the first crossbeam of the lower folding member is wider than the first crossbeam of the upper folding member, so that two first fixing rings of the lower folding member are disposed outside two first fixing rings of the upper folding member; the two first fixing rings of the upper folding member and the two first fixing rings of the lower folding member overlap with each other through the rotation of the lower folding member, and the first flange type self-lubricating bearing is attached to an inner side of each of the two first fixing rings of the upper folding member; a threaded hole is disposed on an inner side of each of the two first fixing rings of the upper folding member, and the first flange type self-lubricating bearing is fixed in the threaded hole by screws;

a first side of the connecting ring of the upper folding member and the lower folding member, facing the second inner arm, comprises a square hole to receive the driven gear shaft, thereby limiting a radial rotation of the upper folding member and the lower folding member, so that the upper folding member and the lower folding member is only rotatable with one of the two driven gear shafts; the driven output shafts rotate to fold the upper folding member and lower folding member inward; the fixed pressure cover is disposed on a second side of the connecting ring of the upper folding member and the lower folding member; the fixed pressure cover, the driven output shaft, and the connecting ring are fixed together through fixing screws thus preventing an axial movement of the upper folding member and the lower folding member; the first mounting base comprises two first fixing shafts which are mutually symmetrical, and the two first fixing shafts extends outside the first fixing ring for installing folding members;

inner sides of the first outer arm and the first inner arm and inner sides of the second outer arm and the second inner arm of the upper folding member and the lower folding member are all provided with clamping grooves and L-shaped sliding grooves; a row of fixed threaded holes are disposed on back sides of the first outer arm, the first inner arm, the second outer arm, and the second inner arm, and the back sides are adjacent to the inner sides;

the first clamping member comprises a sliding block, a lower clamping plate, an upper clamping plate, a rotating shaft, an intermediate pressure plate, and a plurality of fixing bolts;

upper parts of the upper clamping plate and the lower clamping plate comprise a plurality of threaded holes for fixed connection of the upper clamping plate and the lower clamping plate; a lower part of the upper clamping plate and a middle part of the lower clamping plate comprise a shaft groove for receiving the rotating shaft; a lower part of the lower clamping plate comprises a plurality of threaded holes, and a bottom part of the lower clamping plate comprises a rectangular opening; the intermediate pressure plate and an ultra-thin metal strip are disposed through the rectangular opening;

two ends of the rotating shaft comprise umbrella-shaped protrusions, and an inner side of the sliding block comprises an umbrella-shaped groove configured to cooperate with the umbrella-shaped protrusions at two ends of the rotating shaft to enable the rotating shaft to rotate in the sliding block; an outer side of the sliding block comprises a bulge that matches the L-shaped sliding grooves, so that the sliding block is flexibly clamped inside the L-shaped sliding grooves; the first clamping member is adjustable up and down between the first outer arm and the first inner arm, and between the second inner arm and the second outer arm according to a size requirement of the ultra-thin metal strip to be tested; sliding blocks on both sides of the first clamping member are fixed by tightening screws, thereby fixing the first clamping member; the first adjusting ring has a cross-section in the shape of an "Ω", and two ends of the first adjusting ring are respectively disposed in the clamping grooves; the first adjusting ring is adjusted according to requirements and a folding diameter of the ultra-thin metal strip to be tested;

the first diameter adjustment module comprises an adjustment plate, a folding bar, and a support base; the adjustment plate comprises two cross-shaped plates, a connecting rod, and a second fixing shaft; the connecting rod is fixedly disposed on inner centers of the two cross-shaped plates, and the second fixing shaft is fixedly disposed on outer centers of the two cross-shaped plates; the connecting rod and the second fixing shaft are coaxial; an inner side of each of four top ends of each of the two cross-shaped plates comprises a chute for receiving the folding bar; a limiting plate is movably disposed in the chute to fix the folding bar on a corresponding top end of each of the two cross-shaped plates; the second fixing shaft comprises two locking through holes perpendicular to each other to form a "+" shape, corresponding to the four top ends of each of the cross-shaped plates; the folding bar are four in number with different diameters, and comprises a first folding bar, a second folding bar, a third folding bar, and a fourth folding bar;

the support base comprises a U-shaped base and two end covers; two top ends of the U-shaped base comprises two first mounting grooves, respectively, and the second fixing shaft is disposed in the two first mounting grooves; a lower part of each of the two end covers comprises a second mounting grooves, and two second mounting grooves correspond to the two first mounting grooves, respectively; a top part of each of the two end covers comprises two tap holes and a locking pin hole with the same diameter as the locking through holes for receiving a locking pin; the two end covers are fixed on the U-shaped base through tightening screws; the locking pin passes through the locking pin hole and enters one of the locking through holes of the second fixing shaft to prevent a radial rotation of the adjustment plate;

the expansion module comprises a second driver module without a servo motor, a second folding module, a second diameter adjustment module, a first expansion member and a second expansion member; the second driver module without a servo motor is in transmission connection to another end of the driving gear shaft of the drive gearbox through the coupler, so that a power of the expansion module is output forward; the first expansion member and the second expansion member each comprise an upper expansion part and a lower expansion part; the upper expansion part and the lower expansion part each comprise a second crossbeam, a third outer arm, a fourth outer arm, and a second fixing ring; the second fixing ring is fixedly disposed on lower ends of the third outer arm and the fourth outer arm; the second crossbeam of the lower expansion part is wider than the second crossbeam of the upper expansion part, so that two second fixing rings of the lower expansion part are disposed outside two second fixing rings of the upper expansion part; the two second fixing rings of the upper expansion part and the two second fixing rings of the lower expansion part overlap with each other, and a second flange type self-lubricating bearing is attached to an inner side of the two second fixing rings of the third outer arm and the fourth outer arm of the upper expansion part; a threaded hole is disposed on an inner side of each of the two second fixing rings of the upper expansion part, and the second flange type self-lubricating bearing is fixed in the threaded hole by screws; a second mounting base is disposed on an outer side of each of the two second fixing rings to fix the first expansion member and the second expansion member; the expansion module further comprises a second clamping member and a second adjusting ring which are disposed the same as that in the first folding module; the first expansion member and the second expansion member are respectively disposed on two sides of the first folding module, and are respectively fixed on corresponding second mounting bases; the upper expansion part is connected to the upper folding member through a first connection plate, and the lower expansion part is connected to the lower folding member through a second connection plate, so that the upper expansion part and the upper folding member of the first folding module rotate coaxially, and the lower expansion part and the lower folding member of the first folding module rotate coaxially, thereby achieving expansion and extension of the first folding module in two directions;

the first diameter adjustment module is disposed behind the first folding module, and an axis of the folding bar of the first folding module is coaxial to an axis of the first flange type self-lubricating bearing in the first fixing ring of the first folding module; the first diameter adjustment module is disposed between the first outer arm and the first inner arm, between the second inner arm and the second outer arm of the first folding module, and between the third outer arm and the fourth outer arm of the first expansion member and the second expansion member of the expansion module.

2. The device of claim 1, wherein a middle part of the first crossbeam is arc-shaped to avoid the driving gear shaft and the coupler.

3. The device of claim 1, wherein the first connection plate and the second connection plate are disposed between the first crossbeam and the second crossbeam.

4. The device of claim 1, wherein a strain gauge is disposed inside the first diameter adjustment module to measure stress-strain data of the ultra-thin metal strip.

5. The device of claim 1, wherein the expansion module is extended in multiple directions through couplers, and a number of extensions is limited by a number of samples to be tested and working parameters of the servo motor.

6. The device of claim 1, wherein a control system of the servo motor of the first driver module is connected to a computer to set a folding angle and a folding speed of the ultra-thin metal strip, to complete tests under different working conditions.

7. The device of claim 1, wherein the ultra-thin metal strip comprises a stainless steel ultra-thin strip, copper ultra-thin strip, titanium ultra-thin strip, or a composite ultra-thin strip.

8. The device of claim 1, wherein the frame is an aluminum profile frame.

9. The device of claim 1, wherein a cross-section of the first and second connection plate is L-shaped.

\* \* \* \* \*